US012770743B1

(12) United States Patent
Carbone et al.

(10) Patent No.: US 12,770,743 B1
(45) Date of Patent: Oct. 20, 2026

(54) SYSTEMS AND METHODS FOR LINKING STRUCTURED DATA ACROSS MULTIPLE DATABASES

(71) Applicant: Veeva Systems Inc., Pleasanton, CA (US)

(72) Inventors: Michael Lucas Carbone, Toronto (CA); Matthew Zimmerman, Elgin, IL (US)

(73) Assignee: Veeva Systems Inc., Pleasanton, CA (US)

( * ) Notice: Subject to any disclaimer, the term of this patent is extended or adjusted under 35 U.S.C. 154(b) by 2 days.

(21) Appl. No.: 19/170,047

(22) Filed: Apr. 3, 2025

(51) Int. Cl.
*G06F 16/00* (2019.01)
*G16H 50/70* (2018.01)
*G16H 70/40* (2018.01)

(52) U.S. Cl.
CPC ............ *G16H 70/40* (2018.01); *G16H 50/70* (2018.01)

(58) Field of Classification Search
None
See application file for complete search history.

(56) References Cited

U.S. PATENT DOCUMENTS

2009/0158211 A1* 6/2009 Gogolak ................ G16H 50/70 715/811
2009/0319299 A1* 12/2009 De Vries ................ G16H 15/00 705/3
2012/0089418 A1* 4/2012 Kamath ................ G16H 70/40 705/3
2014/0122523 A1* 5/2014 Aggarwal ............ G06F 16/245 707/769
2021/0209549 A1* 7/2021 Bornstein .............. G06F 16/22

* cited by examiner

*Primary Examiner* — Anhtai V Tran

(57) ABSTRACT

A method for linking structured data across a first repository of a first circuit and a second repository of a second circuit. The method further includes querying the first repository based on the adverse event data to select first structured medical product data of the first repository. The first structured medical product data includes an identifier. The first structured medical product data is associated with a first data structure. The method further includes outputting the identifier of the first structured medical product data. The method further includes querying the second repository based on the identifier to select second structured medical product data of the second repository. The second structured medical product data is associated with a second data structure. The method further includes generating, by the second circuit, a product quality data record including at least a portion of the second structured medical product data.

20 Claims, 11 Drawing Sheets

SYSTEMS AND METHODS FOR LINKING STRUCTURED DATA ACROSS MULTIPLE DATABASES

TECHNICAL FIELD

The present disclosure relates to systems and methods for linking structured data across multiple databases.

BACKGROUND

Researchers, scientists, industry players, academics, government regulators, and other stakeholders are increasingly in need of efficient and simple ways to automatically link and utilize uniquely-structured data from multiple databases.

SUMMARY

One embodiment relates to a method for linking structured data across a first repository of a first circuit and a second repository of a second circuit. The method includes receiving, by a first circuit associated with a first application, adverse event data including an adverse event code and identifying a medical product. The method further includes querying, by the first circuit, the first repository based on the adverse event data to select first structured medical product data of the first repository. The first structured medical product data includes an identifier. The first structured medical product data is associated with a first data structure. The method further includes generating, by the first circuit, a case dataset including the adverse event code and at least a portion of the first structured medical product data. The method further includes outputting, by the first circuit, the identifier of the first structured medical product data. The method further includes receiving, by a second circuit associated with a second application, the identifier. The method further includes querying, by the second circuit, the second repository based on the identifier to select second structured medical product data of the second repository. The second structured medical product data includes the identifier. The second structured medical product data is associated with a second data structure. The method further includes generating, by the second circuit, a product quality data record including at least a portion of the second structured medical product data.

Another embodiment relates to a method for linking structured data across a first repository of a first circuit and a second repository of a second circuit. The method includes receiving, by a first circuit associated with a first application, a product quality notification identifying a product quality issue and a medical product. The method further includes querying, by the first circuit, the first repository based on the product quality notification to select first structured medical product data of the first repository. The first structured medical product data includes an identifier. The first structured medical product data is associated with a first data structure. The method further includes generating, by the first circuit, a product quality data record including at least a portion of the first structured medical product data. The method further includes outputting, by the first circuit, the identifier of the first structured medical product data. The method further includes receiving, by a second circuit associated with a second application, the identifier. The method further includes querying, by the second circuit, the second repository based on the identifier to select second structured medical product data of the second repository. The second structured medical product data includes the identifier. The second structured medical product data is associated with a second data structure. The method further includes generating, by the second circuit, a case dataset including at least a portion of the second structured medical product data.

Another embodiment relates to a method for linking structured data across a first repository of a first circuit and a second repository of a second circuit. The method includes receiving, by a first circuit associated with a first application, adverse event data including an adverse event code and identifying a medical product. The method further includes querying, by the first circuit, the first repository based on the adverse event data to select first structured medical product data of the first repository. The first structured medical product data includes an identifier. The first structured medical product data is associated with a first data structure. The method further includes generating, by the first circuit, a case dataset including the adverse event code, a case identifier, and at least a portion of the first structured medical product data. The method further includes outputting, by the first circuit, the identifier of the first structured medical product data and the case identifier. The method further includes receiving, by a second circuit associated with a second application, the identifier. The method further includes querying, by the second circuit, the second repository based on the identifier to select second structured medical product data of the second repository. The second structured medical product data includes the identifier. The second structured medical product data is associated with a second data structure. The method further includes generating, by the second circuit, a product quality data record including at least a portion of the second structured medical product data. The method further includes outputting, by the second circuit, the case identifier. The method further includes receiving, by the first circuit, the case data identifier. The method further includes generating, by the first circuit, a second case dataset including the case identifier and a link to the first case dataset.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
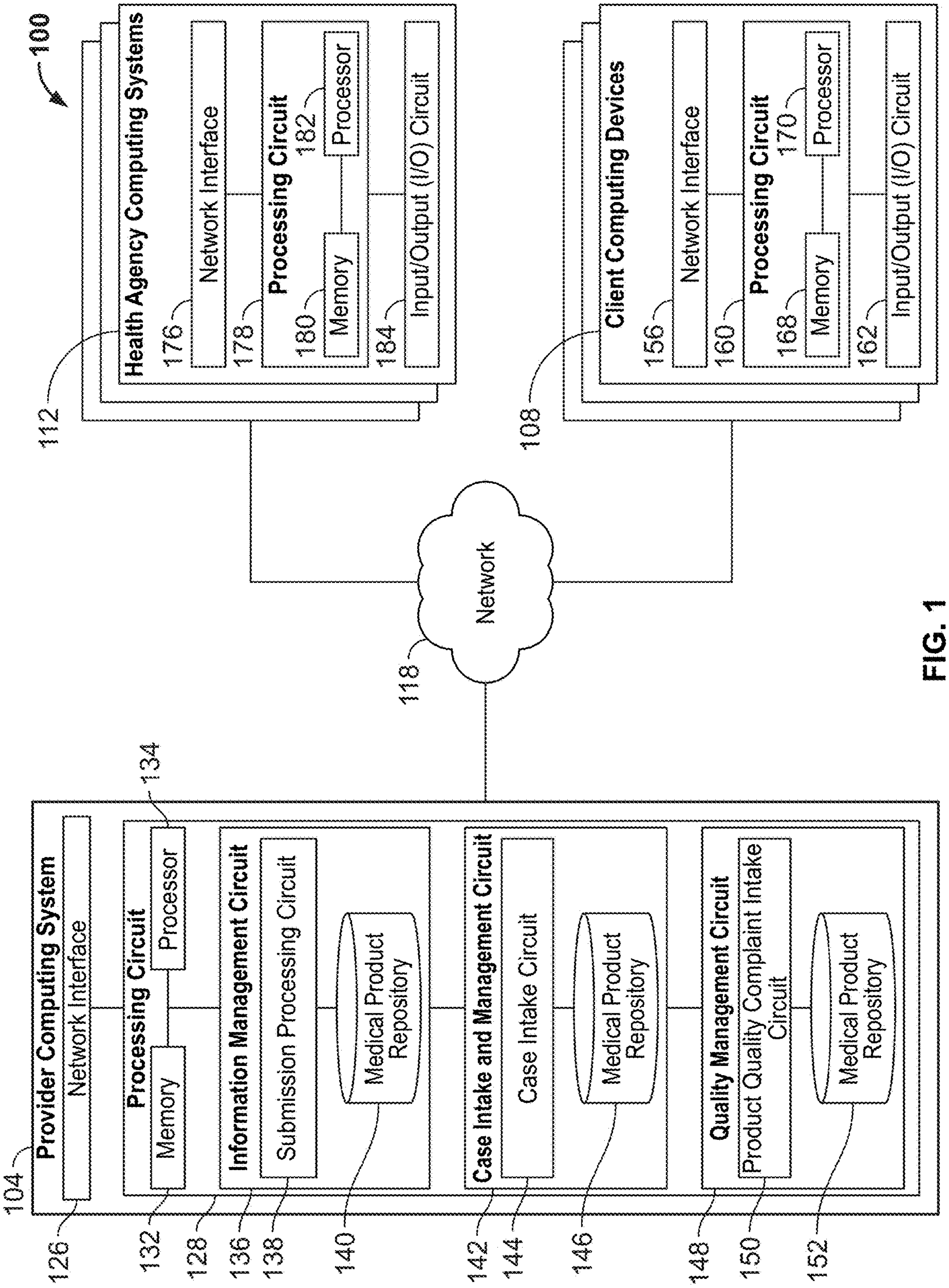
FIG. 1 may be a component diagram of a data linking system, according to an example embodiment.

Referring generally to the figures, systems and methods for linking structured data across multiple databases are disclosed. The systems and methods described herein provide for improved connectivity and less required data transmission between medical data repositories, and thereby provide an improvement to the life sciences industry, as a whole. For instance, because the systems and methods described herein, utilize a medical product identifier to represent the medical product data across each of the repositories, of separate applications, the present systems and methods provide for a technical improvement to data linking and connectivity systems. For instance, instead of transmitting the entire structured medical product data, which may contain numerous fields and complex relationships, the present systems and methods transmit the medical product identifier, a typically small and fixed-length value (e.g., an integer or a UUID). This significantly reduces network bandwidth usage and latency, especially in distributed systems or over networks with limited bandwidth. This is particularly relevant when dealing with large datasets, such as those containing detailed medical imaging or genomic information.

Likewise, the systems and methods described herein effectively decouples the data structures from the transmission mechanism and provide improved data consistency and integrity. For instance, by utilizing the medical product identifier, the present systems and methods provide for greater flexibility in how the medical product data is structured and stored, without impacting the efficiency of data transfer between systems. For example, one system may use a relational database, while another might use a NoSQL document store, but both can communicate effectively using the shared medical product identifier. Likewise, by using a single, consistent identifier, the present systems and methods ensure that all linked data versions refer to the same medical product, reducing the risk of data inconsistencies or errors that can arise from transmitting and reconciling multiple data versions.

Additionally, by utilizing the medical product identifier, the present systems and methods provide a simple, single field, that consistently links the multiple versions of the medical product data such that only the medical product identifier needs to be transmitted across the systems described herein for the correct medical product data to be utilized. In that regard, by utilizing the medical product identifier, the present systems and methods provide a technical improvement to data linking systems and use less memory and processing power. For instance, in typical systems, the entire set of structured medical product data would have to be routed between systems every time a change is made. In comparison, the present systems and methods disseminate the data from a first repository, structure the data according to multiple data structures, and then simply output or route the medical product identifier between systems to communicate, by doing so the present systems require less memory and processing power.

As used herein, the term "event," "medical event," or "adverse event" can include any untoward medical occurrence which happens to either a patient or a subject in a clinical investigation or during regular use of a medical product that has been given to that person. For example, the "event," "medical event," or "adverse event" may encompass any signs which are unfavorable and unexpected for the patient or subject, including any abnormal laboratory findings such as a high blood pressure, a rapid heart rate, etc. The "event," "medical event," or "adverse event" could be symptoms, or a disease temporally associated with the use of a medical product and does not have to have been previously associated with that product. The term "event," "medical event," or "adverse event" can further encompass adverse reactions and serious adverse events such as death, life-threatening adverse experiences, inpatient hospitalization, congenital birth defects, disabilities, etc. Further, each "event," "medical event," or "adverse event" may be defined by the Medical Dictionary for Regulatory Activities (MedDRA) (or other medical code dictionaries) and associated with a specific MedDRA code. Moreover, "event information" "medical event information" "adverse event information" "event data" "medical event data" or "adverse event data" can include information associated with the event such as the date of onset of the event, the date of cessation of the event, the type of event, the dictionary (i.e., digital dictionary, medical dictionary, digital medical dictionary, etc.) or medical term (e.g., MedDRA term), the dictionary or medical code (e.g., MedDRA code), event comments, the outcome of the event, the location of the event (e.g., country where the event occurred), the event duration, patient data for a patient who endured or to which the event occurred, medical products that the patient consumed and/or dosages for the consumed medical products, the event rank, event contacts, the event type, and any associated event documents.

As used herein, the term "case" or "case dataset" can include an Individual Case Safety Report (ICSR) as defined by the standard ISO/HL7 27953 of the International Standards Organization (ISO) as well as any past or future standards governing ICSRs of the ISO, the World Health Organization (WHO), the Food and Drug Administration (FDA), the European Medicines Agency (EMA), or other national health agencies governing ICSRs. Moreover, "case information" "case data" or "case dataset" can include information associated with or included in the case such as adverse event data, case contact data, case identifier (e.g., case worldwide ID (WWID), case number, etc.), case priority data, case seriousness data, case documents, medical product data, medical product registrations, patient data, and other data associated with a case as defined by the standard ISO/HL7 27953 as well as any past or future standards governing ICSRs of the ISO, the WHO, the FDA, the EMA, or other national health agencies governing ICSRs.

Similarly, as used herein "structured data" can include data such as case data, adverse event data, medical product data, or regulatory data which is structured or arranged in a specific data structure. For instance, "structured data" may include medical product data which is structured according to a data schema (e.g., an inbound integration data schema, and outbound integration data schema, etc.). In another instance, "structured data" may include product quality data which is structured according to a data schema and includes a product quality issue. In one example, the systems and methods described herein may receive unstructured data (e.g., unstructured regulatory data, unstructured medical product data, etc.) and structure the unstructured data based on a data schema to generate structured data.

Referring now to FIG. 1, a system 100 for linking structured data across repositories is shown, according to an example embodiment. The system 100 includes a provider computing system 104, multiple client computing devices 108, and multiple health agency computing systems 112 connected by a secure network (e.g., a network 118).

The network 118 communicably and operably couples the provider computing system 104, the client computing devices 108, and the health agency computing systems 112 such that communicable and operable computing may be provided between the provider computing system 104, the client computing devices 108, and the health agency computing systems 112 over the network 118. In various embodiments, the network 118 includes any combination of a local area network (LAN), an intranet, the Internet, or any other suitable communications network, directly or through another interface.

The provider computing system 104 may be operated and managed by a provider (e.g., a software as a service (SaaS) provider, a cloud services provider, a software provider, a service provider, etc.) and may include a computer system (e.g., one or more servers (e.g., a cloud computing server) each with one or more processing circuits). In some embodiments, the provider computing system 104 may act as a host and provide an application (e.g., a web-based application, a mobile application, etc.) to the client computing device 108 over the network 118 in response to authenticating the respective computing device. For example, the provider computing system 104 may receive authentication data (e.g., a username and corresponding password, a limited-use key, a two-factor authentication code or key, etc.) from one of the client computing devices 108. The provider computing system 104 may then authenticate the client computing device 108 based on the authentication data and provide an application to the client computing device 108 over the network 118. In some examples, the provider computing system 104 may be a multi-tenant system where various elements of hardware and software may be shared by one or more customers. In a multi-tenant system, a user is typically associated with a particular customer. In one example, a user (e.g., of the client computing device 108) could be an employee of one of a number of (pharmaceutical) companies which are tenants, or customers, of the provider computing system 104.

In some embodiments, the provider computing system 104 may run on a cloud computing platform. Users can access content on the cloud independently by using a virtual machine image or purchasing access to a service maintained by a cloud repository provider.

In some embodiments, the provider computing system 104 may be provided as Software as a Service ("SaaS") to allow users to access the provider computing system 104 with a thin client.

As shown, the provider computing system 104 may include a network interface 126, a processing circuit 128, and a shared connection repository 130. In some embodiments, the provider computing system 104 may include an input/output circuit (e.g., similar to (e.g., the same as) an input/output circuit 162 as will described further herein).

The network interface 126 is structured to establish connections with the client computing devices 108 and the health agency computing systems 112 by way of the network 118. The network interface 126 includes program logic and/or hardware-based components that connect the provider computing system 104 to the network 118. For example, the network interface 126 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver).

In some embodiments the network interface 126 may include AS2 gateway logic (not shown) that includes programmable instructions that facilitate communication (transmission and receipt) using the AS2 Gateway communication protocol (as specified in Request for Comment (RFC) 4130) over the network 118 via the network interface 126. For example, using the AS2 gateway logic, the network interface 126 may transmit or receive files (e.g., the source file, a case, etc.) or other data to the health agency computing systems 112 and/or the client computing devices 108 using the AS2 Gateway protocol.

In some embodiments, the network interface 126 may include electronic Common Technical Document (eCTD) logic (not shown) that includes programmable instructions that facilitate communication (transmission and receipt) using the eCTD protocol (as specified by the FDA in the eCTD guidance or by other health agencies) over the network 118 via the network interface 126. For example, using the eCTD logic, the network interface 126 may transmit or receive files (e.g., the source file, a case, etc.) or other data to the health agency computing systems 112 and/or the client computing devices 108 using the eCTD communication protocol.

In some embodiments, the network interface 126 includes the hardware and machine-readable media structured to support communication over multiple channels of data communication (e.g., wireless, Bluetooth, near-field communication (NFC). In some embodiments, the network interface 126 includes cryptography logic and capabilities to establish a secure communications session.

The processing circuit 128, as shown, comprises a memory 132, a processor 134, an information management circuit 136 (also referred to as a regulatory information management (RIM) circuit 136), a case intake and management circuit 142, and a quality or product quality management circuit 148. The memory 132 includes one or more memory devices (e.g., RAM, NVRAM, ROM, flash memory, hard disk storage, etc.) that store data and/or computer code for facilitating the various processes described herein. That is, in operation and use, the memory 132 stores at least portions of instructions and data for execution by the processor 134 to control the processing circuit 128. The memory 132 may be or include tangible, non-transient volatile memory and/or non-volatile memory. The processor 134 may be implemented as a general-purpose processor, an application specific integrated circuit (ASIC), one or more field programmable gate array (FPGAs), a digital signal processor (DSP), a group of processing components or other suitable electronic processing components.

As described herein, the information management circuit 136 is structured or configured to receive regulatory data including medical product data from one of the client computing devices 108, intake and structure the regulatory data, and generate a submission to one or more of the health agency computing systems 112. For instance, the information management circuit 136 may be a RIM circuit 136 that receives regulatory data such as medical product data; preclinical data such as data from animal studies that tested the medical product; pharmacology and toxicology studies associated with the medical product; chemistry, manufacturing and control (CMC) data including information about the medical products chemical composition as well as the manufacturing process and quality control procedures that will be used to create the medical product; clinical study data such as foreign clinical study data; and the like. The information management circuit 136 may receive the regulatory data and generate a regulatory submission based on and/or including the regulatory data. For instance, the information management circuit 136 may generate submission such as an investigational new drug application (IND) or a new drug application (NDA) and provide the submission to one of the health agency computing system 112. Then, at a later time, the information management circuit 136 may receive medical product data associated with a registration such as a medical product registration or a clinical study registration from the respective health agency computing system 112. The information management circuit 136 may receive the medical product data, structure the medical product data, and store the structured medical product data in a first medical product repository 140. In one example, the information management circuit 136 may be associated with a first application (e.g., be an instance of Vault RIM®) such as a RIM application.

Additionally, the information management circuit 136 may communicate and/or interface with the case intake and management circuit 146 and/or the quality management circuit 148 to provide received medical product data (e.g., medical product identifier, medical product dosage, medical product type (e.g., medical device, vaccine, drug, etc.), medical product packaging type (e.g., bottle, syringe, etc.), etc. For instance, the information management circuit 136 may provide at least a portion of the medical product data stored in the first medical product repository 140 to the case intake and management circuit 142 and the quality management circuit 148.

As described herein, each circuit of the provider computing system 104 may be disposed across one or more servers. For instance, the information management circuit 136 may operate on a first server computing device; the case intake and management circuit 142 may operate on a second server computing device; and the quality management circuit 148 may operate on a third server computing device, each server distributed across one or more locations. In this regard, each circuit of the processing circuit 128 may be a separate instance of a Virtual Private Clouds (VPC), thereby providing a certain level of isolation between the information management circuit 136, the case intake and management circuit 146, and the quality management circuit 148 using the resources (e.g., the memory 136 and the processor 140). For instance, the provider computing system 104 may include multiple information management circuits 136, multiple case intake and management circuits 146, and multiple quality management circuits 148.

As shown, the information management circuit 136 may include a submission processing circuit 138 and a first medical product repository 140. In some embodiments, the information management circuit 136 may include a certificate or key repository (not shown) for storing a certificate or key (pair). The submission processing circuit 138 may be configured or structured to receive the regulatory data from one or more of the client computing devices 108 and store the regulatory data in the medical product repository 140. In other embodiments, the information management circuit 136 may include additional repositories, and the submission processing circuit 138 may store a portion of the regulatory data in the medical product repository 140 and other regulatory data in the additional repositories. Further, the submission processing circuit 138 may generate a submission such as an eCTD XML file including one or more portions of the regulatory data. For instance, the submission processing circuit 138 may generate an IND as an eCTD XML file including the one or more portions of the regulatory data. Then, via the network interface 126, the submission processing circuit 138 may submit or transmit the eCTD XML file to the respective health agency computing device(s) 112.

In some embodiments, in response, the submission processing circuit 138 may receive medical product data associated with a medical product or study registration from the health agency computing device(s) 112. For instance, in response to the IND, the submission processing circuit 138 may receive an IND approval letter including an IND number, a medical product name, approval conditions, clinical trial requirements, reporting and monitoring obligations, and the like. Then, the submission processing circuit 138 may generate a medical product data record including at least a portion of the data included in the IND approval letter. In some embodiments, the submission processing circuit 138 may share/output the medical product data of the medical product repository 140. In other embodiments, another circuit of the information management circuit 136 (not shown) may share/output the medical product data of the medical product repository 140.

The (first) medical product repository 140 may be repository (e.g., a database) that is structured or configured to receive, store, and manage the structured medical product data of medical products through interaction with the submission processing circuit 138. For example, the submission processing circuit 138 may receive regulatory data from the client computing devices 108 to prepare submissions to the health agency computing systems 112. The regulatory data may include medical product data such as an organization or client that owns the medical product, a substance or chemical formula of the medical product, a medical product identifier, a dosage of the medical product, a type of the medical product, and the like. The medical product repository 140 may receive the medical product data and store the medical product data therein. In some embodiments, in response to receiving medical product data, the medical product repository 140 may output at least a portion of the medical product data to the case intake and management circuit 142 and/or the quality management circuit 148.

The medical product repository 140 can be structured according to various database types, such as, relational, hierarchical, network, flat, point-in time, and/or object relational. In some embodiments, the medical product repository 140 includes a plurality of nonvolatile/non-transitory storage media such as solid-state storage media, hard disk storage media, virtual storage media, cloud-based storage drives, storage servers, and/or the like. In some embodiments, the provider computing system 104 may include a medical product repository 140 for each customer or sponsor, thereby keeping the medical product data of each customer separate.

As described herein, the case intake and management circuit 142 is structured or configured to receive, generate, store, and manage case datasets. For instance, the case intake and management circuit 142 may be configured or structured to receive medical product data and store the medical product data in a (second) medical product repository 142. The case intake and management circuit 142 may then receive or retrieve adverse event data associated with an adverse event from a trusted source (one of the client computing devices 108, one of the health agency computing systems 112, etc.). Further, the case intake and management circuit 142 may match the adverse event data with medical product data of the (second) medical product repository 146, generate a case dataset including case data, and store the case dataset within a case repository (not shown). In one example, the case intake and management circuit 142 may be associated with a second application (e.g., be an instance of Vault Safety®) such as a pharmacovigilance case processing and reporting application. As shown, the case intake and management circuit 142 includes the case intake circuit 144 and the medical product repository 146.

The case intake circuit 144 is configured or structured to receive adverse event data, match the adverse event data with the medical product data, and generate a case dataset including at least a portion of the adverse event data and the medical product data. For instance, the case intake circuit 144 may receive a source file including adverse event data associated with an adverse event (e.g., heart attack) and a medical product (e.g., drug x). Accordingly, the case intake circuit 144 may search the medical product repository 146 for a medical product that matches the medical product of the adverse event data and return the matching medical product data (e.g., a registration for drug x, a UID of drug x, one or more substance(s) included in drug x, etc.). The case intake circuit 144 may then generate a case dataset including at least a portion of the adverse event data and the medical product data. Further, the case intake circuit 144 may then generate an electronic submission package and output at least a portion of the case dataset in the electronic submission package to one of the health agency computing systems 112 or the client computing devices 108. In this regard, the case intake circuit 144 may provide for the intake, processing, and submission of case datasets to health authorities.

In some embodiments, the case intake and management circuit 144 may receive medical product data from the information management circuit 136 and store the medical product data therein. Likewise, the case intake and management circuit 144 may output potential Product-quality complaint(s) to the quality management circuit 148, as will be described further herein. In other embodiments, a different circuit (not shown) of the case intake and management circuit 142 may communicate with the other circuits of the processing circuit 128.

The (second) medical product repository 146 may be a repository (e.g., a database) that is structured or configured to receive, store, and manage medical product data of medical products through interaction with the information management circuit 136. For example, the case intake and management circuit 142 may receive medical product data from the information management circuit 136 and store it in the medical product repository 146. The medical product repository 146 may receive the medical product data and store the medical product data therein. In some embodiments, the medical product repository 146 may receive the medical product data as a part of one or more data records. In this regard, the medical product repository 146 may store the data records therein.

The medical product repository 146 can be structured according to various database types, such as, relational, hierarchical, network, flat, point-in time, and/or object relational. In some embodiments, the medical product repository 146 includes a plurality of nonvolatile/non-transitory storage media such as solid-state storage media, hard disk storage media, virtual storage media, cloud-based storage drives, storage servers, and/or the like. In some embodiments, the provider computing system 104 may include a medical product repository 146 for each customer or sponsor, thereby keeping the medical product data of each customer separate.

As described herein, the quality management circuit 148 is structured or configured to receive, generate, store, and manage quality product data records. For instance, the quality management circuit 148 may be configured or structured to receive medical product data and store the medical product data in a (third) medical product repository 151. The quality management circuit 148 may then receive or retrieve a quality management notification associated with a product quality issue from a trusted source (one of the client computing devices 108, one of the health agency computing systems 112, etc.). Further, quality management circuit 148 may match the product quality notification with medical product data of the (third) medical product repository 146, generate a product quality data record, and store the product quality data record within a product quality repository (not shown). In one example, the quality management circuit 148 may be associated with a third application (e.g., be an instance of Veeva Quality®) such as a product quality control and management application. As shown, the quality management circuit 148 includes the product quality complaint intake circuit 150 and the medical product repository 152.

The product quality complaint intake circuit 150 is configured or structured to receive product quality notifications, match the product quality notification(s) with medical product data, and generate a product quality data record including at least a portion of the medical product data. For instance, the product quality complaint intake circuit 150 may receive a source file including product quality notification associated with a quality issue (e.g., broken seal, miscolored product, broken packaging, etc.) and a medical product (e.g., drug x). Accordingly, the quality management circuit 148 may search the medical product repository 152 for a medical product that matches the medical product of the product quality notification and return the matching medical product data (e.g., a registration for drug x, a UID of drug x, one or more substance(s) included in drug x, etc.). The product quality complaint intake circuit 150 may then generate a product quality data record including at least a portion of the quality issue and the medical product data. In some embodiments, the product quality complaint intake circuit 150 may then output the product quality data record (e.g., to one of the health agency computing devices 112, to one of the client computing devices 108, etc.).

In some embodiments, the product quality complaint intake circuit 150 may receive medical product data from the information management circuit 136 and store the medical product data therein. Likewise, the product quality complaint intake circuit 150 may output potential adverse events to the case intake and management circuit 142, as will be described further herein. In other embodiments, a different circuit (not shown) of the quality management circuit 148 may communicate with the other circuits of the processing circuit 128.

The (third) medical product repository 152 may be a repository (e.g., a database) that is structured or configured to receive, store, and manage medical product data of medical products through interaction with the information management circuit 136. For example, the quality management circuit 148 may receive medical product data from the information management circuit 136 and store it in the medical product repository 152. The medical product repository 152 may receive the medical product data and store the medical product data therein. In some embodiments, the medical product repository 152 may receive the medical product data as a part of one or more data records. In this regard, the medical product repository 152 may store the data records therein.

The medical product repository 152 can be structured according to various database types, such as, relational, hierarchical, network, flat, point-in time, and/or object relational. In some embodiments, the medical product repository 152 includes a plurality of nonvolatile/non-transitory storage media such as solid-state storage media, hard disk storage media, virtual storage media, cloud-based storage drives, storage servers, and/or the like. In some embodiments, the provider computing system 104 may include a medical product repository 152 for each customer or sponsor, thereby keeping the medical product data of each customer separate.

Each of the sets of medical product data may be structured differently (e.g., according to a different data structure or schema) but linked via the medical product identifier. In this regard, by utilizing the medical product identifier, the present systems and methods provide a simple, single field, that consistently links the multiple versions of the medical product data such that only the medical product identifier needs to be transmitted across the systems described herein for the correct medical product data to be utilized. In that regard, by utilizing the medical product identifier, the present systems and methods provide a technical improvement to data linking systems and use less memory and processing power. For instance, in typical systems, the entire set of structured medical product data would have to be routed between systems every time a change is made. In comparison, the present systems and methods disseminate the data from a first repository, structure the data according to multiple data structures, and then simply output or route the medical product identifier between systems to communicate, by doing so the present systems require less memory and processing power.

Still referring to FIG. 1, the client computing devices 108 can each be any type of computing device or computing system. For instance, each client computing device 108 can be one or more of a mobile phone, a tablet computer, a laptop computer, a smart watch, a server computer system, or any other internet-connected device. In operation, the client computing devices 108 may communicate and interface with the provider computing system 104 via the network 118 to provide regulatory data to the information management circuit 136; source files including adverse event data to the case intake and management circuit 142; and/or product quality notifications to the quality management circuit 148. As shown, each client computing device 108 may include a network interface 156, a processing circuit 160, and the input/output (I/O) circuit 162.

The network interface 156 is structured to establish connections with the provider computing system 104 by way of the network 118. The network interface 156 includes program logic and/or hardware-based components that connect the client computing device 108 to the network 118. For example, the network interface 156 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 156 includes the hardware and machine-readable media structured to support communication over multiple channels of data communication (e.g., wireless, Bluetooth, near-field communication (NFC). In some embodiments, the network interface 156 includes cryptography logic and capabilities to establish a secure communications session.

The processing circuit 160, as shown, comprises a memory 168 and a processor 170. The memory 168 includes one or more memory devices (e.g., RAM, NVRAM, ROM, flash memory, hard disk storage, etc.) that store data and/or computer code for facilitating the various processes described herein. That is, in operation and use, the memory 168 stores at least portions of instructions and data for execution by the processor 170 to control the processing circuit 160. The memory 168 may be or include tangible, non-transient volatile memory and/or non-volatile memory. The processor 170 may be implemented as a general-purpose processor, an application specific integrated circuit (ASIC), one or more field programmable gate array (FPGAs), a digital signal processor (DSP), a group of processing components or other suitable electronic processing components.

The I/O circuit 162 is structured to receive communications from and provide communications to the user of the client computing device 108 (e.g., the user). In this regard, the I/O circuit 162 is structured to exchange data with the processing circuit 160 to provide output to the user and to receive input from the user. As a result, the I/O circuit 162 may include a display that may be manipulated by the application. In some embodiments, the I/O circuit 162 may also include a keyboard, a mouse, a joystick, a touch screen, touch areas, soft keys, a microphone, a speaker, a vibration mechanism, a sensor, a RFID scanner, or other input/output devices described herein.

Still referring to FIG. 1, the health agency or authority computing systems 112 can include any type of computing device or computing system and may be associated or managed by a health agency (e.g., the FDA, the EMA, Health Canada, etc.). For instance, at least one of the health agency computing systems 112 may be the Electronics Submission Gateway (ESG) of the FDA through which one or more E2B XML files and/or an FDA 3500A PDF files (e.g., case datasets) may be received from or provided to. In operation, each health agency computing system 112 may communicate with the provider computing system 104 or the client computing devices 108 to send and/or receive one or more case datasets associated with adverse events (e.g., E2B files). Further, the health agency computing system 112 may include a network interface 176, a processing circuit 178, and the input/output (I/O) circuit 184.

The network interface 176 is structured to establish connections with the provider computing system 104 by way of the network 118. The network interface 176 includes program logic and/or hardware-based components that connect the client computing device 108 to the network 118. For example, the network interface 176 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 176 includes the hardware and machine-readable media structured to support communication over multiple channels of data communication (e.g., wireless, Bluetooth, near-field communication (NFC). In some embodiments, the network interface 176 includes cryptography logic and capabilities to establish a secure communications session.

In some embodiments the network interface 176 may include AS2 gateway logic (not shown) that includes programmable instructions that facilitate communication (transmission and receipt) using the AS2 Gateway communication protocol (as specified in Request for Comment (RFC) 4130) over the network 118 via the network interface 176. For example, using the AS2 gateway logic, the network interface 176 may transmit or receive files (e.g., the source file, a case, etc.) or other data from the provider computing system 104 using the AS2 Gateway protocol.

The processing circuit 178, as shown, comprises a memory 180 and a processor 182. The memory 182 includes one or more memory devices (e.g., RAM, NVRAM, ROM, flash memory, hard disk storage, etc.) that store data and/or computer code for facilitating the various processes described herein. That is, in operation and use, the memory 180 stores at least portions of instructions and data for execution by the processor 182 to control the processing circuit 178. The memory 180 may be or include tangible, non-transient volatile memory and/or non-volatile memory. The processor 182 may be implemented as a general-purpose processor, an application specific integrated circuit (ASIC), one or more field programmable gate array (FPGAs), a digital signal processor (DSP), a group of processing components or other suitable electronic processing components.

The I/O circuit 184 is structured to receive communications from and provide communications to the user of the health agency computing system 112 (e.g., the health agency user). In this regard, the I/O circuit 184 is structured to exchange data with the processing circuit 178 to provide output to the user and to receive input from the health agency user. As a result, the I/O circuit 180 may include a display that may be manipulated by the application. In some embodiments, the I/O circuit 180 may also include a keyboard, a mouse, a joystick, a touch screen, touch areas, soft keys, a microphone, a speaker, a vibration mechanism, a sensor, a RFID scanner, or other input/output devices described herein.

Figure 2:
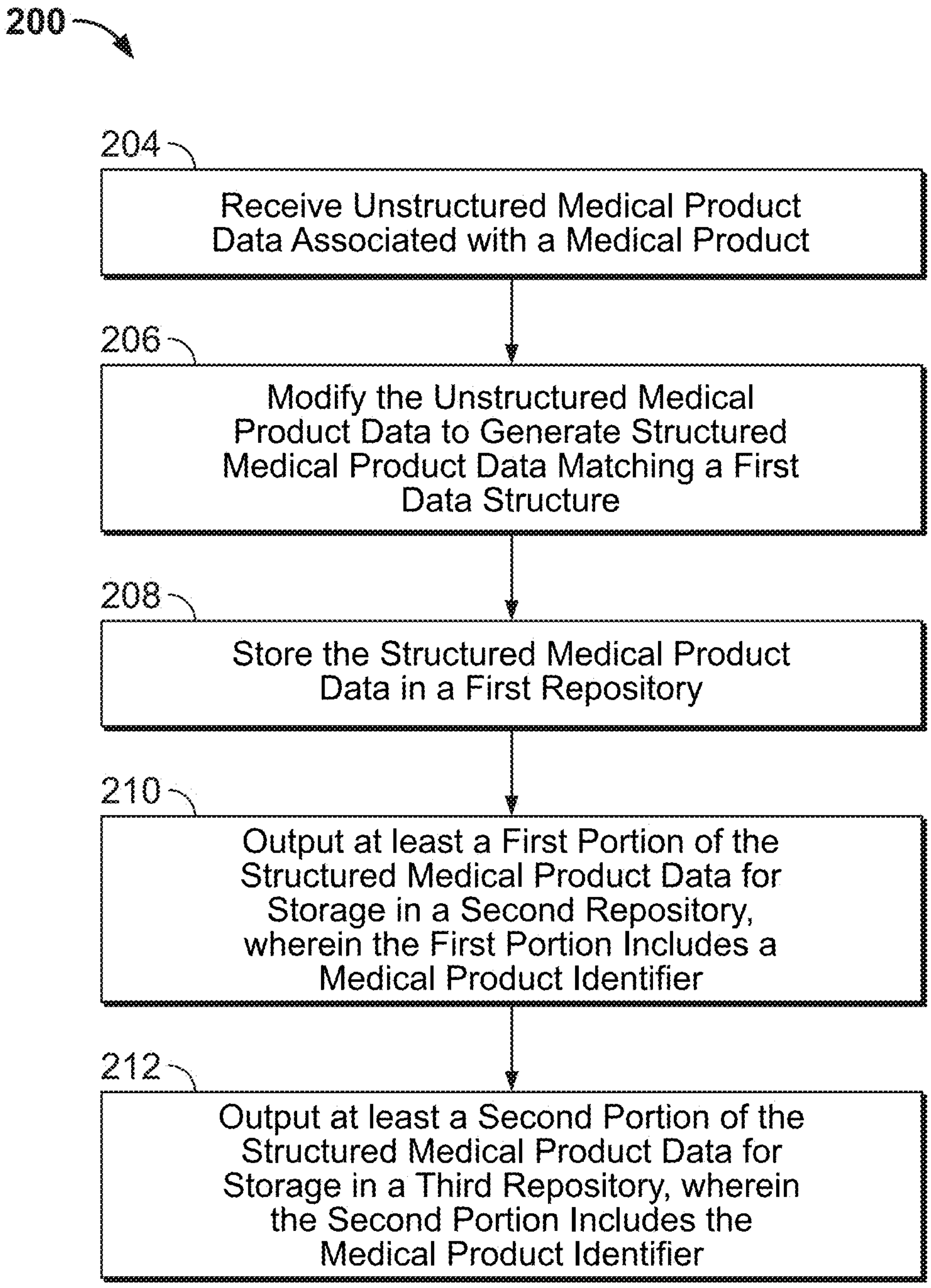
FIG. 2 may be a flow diagram of a method for initially distributing structured data, according to an example embodiment.

Referring now to FIG. 2, a method 200 of initially distributing structured data is shown, according to an example embodiment. Method 200 can be carried out by the system of FIG. 1. More particularly, the method 200 can be carried out by the processing circuit 128 of the provider computing system 104 and through communication with the client computing devices 108 and the health agency computing systems 112.

Method 200 commences at step 204 at which the provider computing system 104 (and more particularly the information management circuit 136) receives medical product data associated with a medical product. For instance, the provider computing system 104 may receive medical product data from one of the client computing devices 108 and/or the health agency computing devices 112.

In some embodiments, the provider computing system 104 may receive a first portion of the medical product data from one of the client computing devices 108 and a second portion of the medical product data from one of the health agency computing devices 112. For instance, the provider computing system 104 may receive regulatory data including the first portion of the medical product data (e.g., tradename of the medical product, medical product dosage, medical product type, etc.), preclinical data including data from animal studies that tested the medical product, pharmacology and toxicology studies associated with the medical product, and the like. The provider computing system 104 may receive the regulatory data (including the first portion of the medical product data) and generate a regulatory submission based on and/or including the regulatory data. For instance, the provider computing system 104 may generate submission such as an investigational new drug application (IND) or a new drug application (NDA) and provide the submission to one of the health agency computing system 112. Then, at a later time, the provider computing system 104 may receive the second portion of the medical product data (e.g., medical product registration number, medical product identifier (national drug code, new drug application number, etc.) associated with a registration such as a medical product registration or a clinical study registration from the respective health agency computing system 112.

In some embodiments, the medical product data may be unstructured. For instance, the medical product data may not include a specified set of fields or values and have no specific structure. For instance, the unstructured medical product data doesn't fit into a row-and-column database structures because it lacks a predefined data model.

Once the provider computing system 104 has received the medical product data, the method 200 proceeds to step 206 at which the provider computing system 104 modifies the unstructured medical product data to generate structured medical product data. The structured medical product data may be modified to match or correspond to a specific data structure or schema. For instance, the provider computing system 104 may determine specific fields and/or records of the first data structure based on the unstructured medical product data and generate the structured medical product data to include the specific fields and/or records. In one example, the structured medical product data may match or correspond to a regulatory information management medical product data schema.

Once the provider computing system 104 has modified the unstructured medical product data to generate structured medical product data, the method 200 proceeds to step 208 at which the provider computing system 104 stores the structured medical product data in the first repository (also referred to as the first medical product repository) 140.

Once the provider computing system 104 has stored the structured medical product data in the first repository 140, the method 200 proceeds to step 210 at which the provider computing system 104 outputs at least a first portion of the structured medical product data for storage in the second repository (also referred to as the second medical product repository) 146. For instance, the information management circuit 136 may output at least a portion of the structured medical product to the case intake and management circuit 142 for storage in the second medical product repository 146. The case intake and management circuit 146 may utilize a different data structure or schema (e.g., a second medical product data schema) than the information management (e.g., a first medical product data schema). Accordingly, the information management circuit 136 may output the portion(s) or fields of the structured medical product data which may be utilized or included in the second medical product data schema, while leaving the other portion(s) or fields which may not be utilized. In some embodiments, the information management circuit 136 may output the entire set of structured medical product data, and the case intake and management circuit 142 may parse the structured medical product data for the portion(s) which match or correspond to the second medical product data schema.

The first portion of the structured medical product data may include a medical product identifier (e.g., a NDC, a new drug application number, a chemical formula, a tradename, etc.) which is used to identify the medical product across the different medical product repositories and medical product data schemas.

Each of the sets of medical product data may be structured differently (e.g., according to a different data structure or schema) but linked via the medical product identifier. In this regard, by utilizing the medical product identifier, the present systems and methods provide a simple, single field, that consistently links the multiple versions of the medical product data and reduces data transmission overhead. For instance, instead of transmitting the entire structured medical product data, which may contain numerous fields and complex relationships, only the medical product identifier, a typically small and fixed-length value (e.g., an integer or a UUID), is transmitted. This significantly reduces network bandwidth usage and latency, especially in distributed systems or over networks with limited bandwidth. This is particularly relevant when dealing with large datasets, such as those containing detailed medical product data.

Once the provider computing system 104 has output the first portion of the structured medical product data, the method 200 proceeds to step 212 at which the provider computing system 104 outputs at least a second portion of the structured medical product data for storage in the third repository (also referred to as the third medical product repository) 152. For instance, the information management circuit 136 may output at least a portion of the structured medical product to the quality management circuit 148 for storage in the third medical product repository 152. The quality management circuit 148 utilize a different data structure or schema (e.g., a third medical product data schema) than the first medical product data schema. Accordingly, the information management circuit 136 may output the portion(s) or fields of the structured medical product data which may be utilized or included in the third medical product data schema, while leaving the other portion(s) or fields which may not be utilized. In some embodiments, the information management circuit 136 may output the entire set of structured medical product data, and the quality management circuit 148 may parse the structured medical product data for the portion(s) which match or correspond to the third medical product data schema.

The second portion of the structured medical product data may include the medical product identifier (e.g., a NDC, a new drug application number, a chemical formula, a tradename, etc.) which is used to identify the medical product across the different medical product repositories and medical product data schemas.

Each of the sets of medical product data may be structured differently (e.g., according to a different data structure or schema) but linked via the medical product identifier. In this regard, by utilizing the medical product identifier, the present systems and methods provide a simple, single field, that consistently links the multiple versions of the medical product data and provides for an optimized memory footprint. For instance, storing and processing only the medical product identifier in transient memory (RAM) is far more efficient than handling the entire dataset. This reduces the memory footprint of the applications and systems involved, allowing for more concurrent operations or the use of less powerful hardware. For example, if a medical product dataset involves megabytes of data, but the identifier is only a few bytes, the memory savings are substantial.

Figure 3:
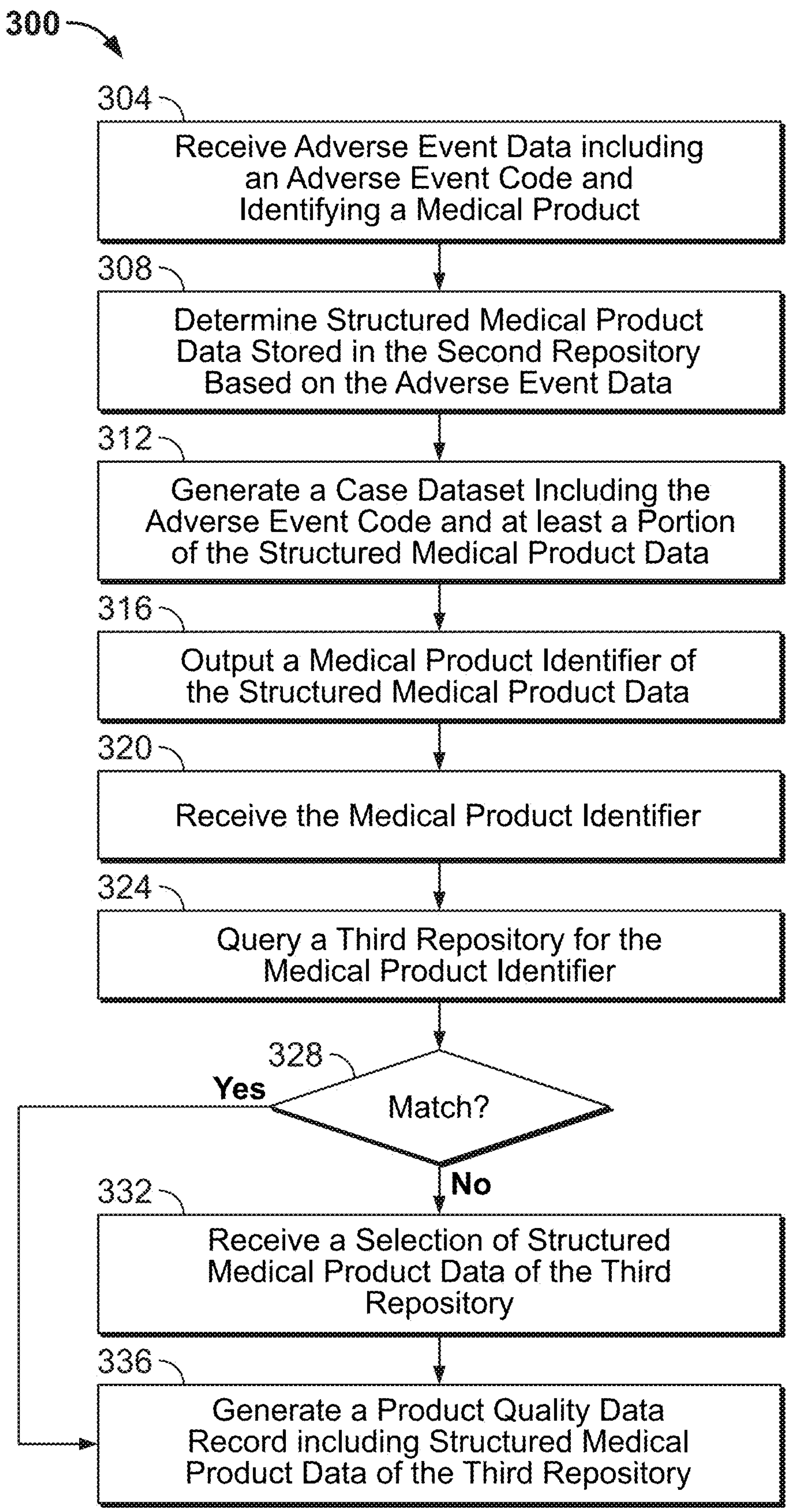
FIG. 3 may be a flow diagram of a method for determining structured data of a third repository based on an identifier of a second repository, according to an example embodiment.

Referring now to FIG. 3, a method 300 determining structured data of a third repository based on an identifier of a second repository is shown, according to an example embodiment. While different overall, it should be understood that any steps or discussion of the method 300 may be applied or included within the methods 200 and 400, and vice versa, and that such combinations are included within the scope of the present disclosure. For example, provider computing system 104 may perform the method 200 to link the medical product across repositories and then perform the method 300 or 400, in response to receiving inbound data. Method 300 can be carried out by the system of FIG. 1. More particularly, the method 300 can be carried out by the processing circuit 128 of the provider computing system 104 and through communication with the client computing devices 108 and the health agency computing systems 112. In some embodiments, steps 304-316 are performed by the case intake and management circuit 142, and steps 320-336 are performed by the quality management circuit 148.

In another example, the provider computing system 104 may perform the method 300 to generate a case dataset and a product quality data record, and then perform the method 400 in response to receiving an update to the product quality data record. For instance, the quality management circuit 148 may receive an update to the product quality data record after interacting with the reporter (e.g., a new adverse event, a new medical product, etc.). Then, in response, the quality management circuit 148 may proceed through the method and update the product quality data record at step 412. Then, at step 416, the quality management circuit 148 may output the medical product identifier, and the case identifier received from the case intake and management circuit 142. Accordingly, in response to receiving new information with a valid case identifier, the case intake and management circuit 142 may generate a new case dataset with a type of follow-up and including a link (e.g., a hyperlink, a uniform resource locator (URL), a reference pointer, etc.) to the first case dataset associated with the case identifier.

Method 300 commences at step 304 at which the provider computing system 104 receives adverse event data associated with an adverse event and a medical product. For instance, the adverse event data may identify or include an adverse event term (e.g., a MedDRA term) and/or code (e.g., a MedDRA term), etc.) for each adverse event. Further, the source file adverse event data may identify a medical product and/or include medical product data (e.g., a medical product identifier, a reported medical product name, a dosage, a strength, a route of administration, etc.) associated with each medical product and/or the adverse event. In some embodiments, the adverse event data may be received from one of the client computing devices 108 or one of the health agency computing systems 112.

In some embodiments, the adverse event data may be received in a source file. In some embodiments, the source file may be an E2B (R2 or R3) XML file received via an AS2 Gateway communication from one of the client computing devices 108 or one of the health agency computing systems 112. In other embodiments, the source file may be at least one of a PDF file, an Excel file, an E2B XML file, CSV file, an email, or other file types described herein. The source file or adverse event data thereof may identify or include the first medical product data, study data (e.g., a study identifier), an adverse event term and code (e.g., a MedDRA term and code), reporter data (e.g., a reporter name, a reporter country, a reporter address or contact information (e.g., email, phone number, IP address, FTP address, etc.)), patient data (e.g., patient initials, patient address or contact information), a report type (e.g., spontaneous, from study, from marketed medical product, etc.), a seriousness of the adverse event, and the like.

Once the provider computing system 104 has received the adverse event data, the method 300 proceeds to step 308 at which the provider computing system 104 determines and selects structured medical product data stored in the second repository 146 based on the adverse event data. For example, the adverse event data may indicate that the patient consumed Y Milliliters of a medical product X on Mar. 23, 2000. At step, 308, the provider computing system 104 may then search or query the second medical product repository 146 for structured medical product data pertaining to medical product X and return the matching structured medical product data. In some embodiments, the structured medical product data may include the first portion(s) received from the information management circuit 138, as described with regard to the method 200.

Once the provider computing system 104 has selected the structured medical product data stored in the second repository 146, the method 300 proceeds to step 312 at which the provider computing system 104 generates a case dataset. The case dataset may be generated to include an identifier (e.g., a unique ID, a worldwide unique ID (WWUID), etc.) at least a portion of the adverse event data and at least a portion of the structured medical data. In some embodiments, after generating the case dataset, the provider computing system 104 may store the case dataset in a case repository (not shown).

In some embodiments, at or after step 312, the provider computing system 104 may be configured to provide the case to one or more of the health agency computing systems 112 and/or the client computing devices 108. In one example, the case may be stored in the form of an E2B XML file and provided to one or more of the health agency computing systems 112 and/or the client computing devices 108 via an AS2 Gateway communication. In some embodiments, the provider computing system 104 may receive an indication or request from the client computing devices 112 to provide the case to one of the health agency computing systems 112, and do so in response. In some embodiments, the provider computing system 104 may automatically provide the case dataset based on a report timeframe of the case. For example, if the case is generated to include a report timeframe of seven days from receipt of the source file and it has been seven days from receipt of the source file, the provider computing system 104 may automatically provide the case to one or more of the health agency computing systems 112 and/or the client computing devices 108.

In some embodiments, prior to step 312, the provider computing system 104 queries or searches a case repository (not shown) to determine one or more potentially matching case datasets substantially matching the adverse event data and medical product data. Then, in response to the provider computing system 104 searching the case repository and not determining or selecting any matches, the method 300 may proceed to step 312.

Once the first repository has generated the case dataset, the method 300 proceeds to step 316 at which the provider computing system 104 (and more particularly the case intake and management circuit 142) outputs a medical product identifier of the structured medical product data. For instance, at step 316, the case intake and management circuit 142 may output the medical product identifier to the quality management circuit 148. As described herein, the case intake and management circuit 142 may correspond to a pharmacovigilance application for the detection and reporting of adverse events, whereas the quality management circuit 148 may correspond to a product quality application for the detection, monitoring, and correction of product quality issues (e.g., broken packaging seals, miscolored capsules, etc.). However, these applications can overlap. For instance, the case intake and management circuit 142 may receive an adverse event report that identifies a product quality issue (e.g., broken packaging which resulted in a patient experiencing nausea, etc.). Accordingly, at step 316, the case intake and management circuit 142, may output data associated with a potential quality management issue to the quality management circuit 148.

In some embodiments, the case intake and management circuit 142 may output the medical product identifier to the quality management circuit 148 in response to receiving a request to do so (e.g., one of the client computing devices 112 via a send button (see FIG. 6A)). In other embodiments, the case intake and management circuit 142 may output the medical product identifier to the quality management circuit 148, in response to a specific criteria being fulfilled (e.g., the case dataset being created and including an adverse event data record with a type of "product quality complaint" (see FIG. 5A), a case dataset entering a specific lifecycle state (e.g., submitted), the case dataset including an adverse event term that matches a specific term (e.g., "discolor," "broken seal," etc.).

In some embodiments, at step 316, the case intake and management circuit 142 may output the medical product identifier and additional data (e.g., a specific date/time on which the adverse event occurred, a note or explanation of the adverse event, the adverse event term and/or code, study data or a study identifier associated with the medical product, etc.). For instance, at step 316, the case intake and management circuit 142 may output the medical product identifier, a case identifier, a description of the adverse event, a reporter name, an initial contact method of the reporter, a date of the adverse event, an awareness date, and the like.

Once the provider computing system 104 (and more particularly the case intake and management circuit 142) has output the medical product identifier, the method 300 proceeds to step 320 at which the provider computing system 104 (and more particularly the quality management circuit 148) receives the medical product identifier. For instance, the case intake and management circuit 142 may transmit the medical product identifier over the network 118 to the quality management circuit 148.

Once the provider computing system 104 (and more particularly the quality management circuit 148) has received the medical product identifier, the method 300 proceeds to step 324 at which the provider computing system 104 searches or queries the third repository 152 for medical product data that matches the medical product identifier. For instance, the medical product identifier may include the NDC 112233. Accordingly, the provider computing system 104 may query or search the third repository 152 for structured medical product data which matches or includes the NDC 112233.

As described herein, the medical product identifier provides for a simple, consistent, representation of the structured medical product data across multiple applications, circuit, and repositories. Accordingly, by utilizing the medical product identifier, the present systems and methods provide a technical improvement to data transmission systems by decreasing the processing load and improving data consistency and integrity. For instance, the processing required to transmit, parse, and handle a single identifier is significantly less than that required for a complex data structure. This translates to lower CPU utilization and faster processing times. For instance, serializing and deserializing complex JSON or XML structures requires considerable processing, whereas handling a simple integer identifier is a trivial operation. Likewise, by using a single, consistent identifier, the system ensures that all linked data versions refer to the same medical product, reducing the risk of data inconsistencies or errors that can arise from transmitting and reconciling multiple data versions.

Once the provider computing system 104 has queried the third repository 152 for the medical product identifier, the method 300 proceeds to step 328 at which the provider computing system 104 determines if there is a match (e.g., a medical product data record/medical product data including the medical product identifier). If there is no match, the method 300 proceeds to step 332 at which the provider computing system 104 receives a selection of structured medical product data of the third repository 152. For instance, in response to there being no match, the provider computing system 104 may generate and output a notification to one of the client computing devices 108. In response, the client computing device 108 may provide a selection or indication of specific structured data of the third repository 148.

In some embodiments, if there is no match at step 328, the provider computing system 104 may query the third repository 152 for a secondary identifier of the medical product. For instance, at step 320, the provider computing system 104 (and more particularly the quality management circuit 148) may receive a secondary identifier of the medical product (e.g., a trade name of the medical product, a substance or set of substances included in the medical product, etc.). The secondary identifier may provide a back-up identifier to be used, when there is no matching medical product identifier.

After step 332, or if the provider computing system 104 determines a match at step 328, the method 300 proceeds to step 336 at which the provider computing system 104 generates a product quality data record including the structured medical product data of the third repository 152. In some embodiments, the product quality data record may include the additional values output by the case intake and management circuit 142 (e.g., the date/time, the narrative of the adverse event, etc.). In some embodiments, after step 336, the provider computing system 104 may output the product quality data record to one of the client computing devices 108 and/or the health agency computing systems 112.

In some embodiments, after generating the product quality data record, the provider computing system 104 (and more particularly the quality management circuit 148) may output an identifier of the product quality data record (e.g., a product quality data record number). For instance, FIG. 6B shows a case page 600 including a quality complaint ID field 628. In this regard, the provider computing system 104 (and more particularly the case intake and management circuit 142) may add the identifier to the case dataset for storage therein.

Figure 4:
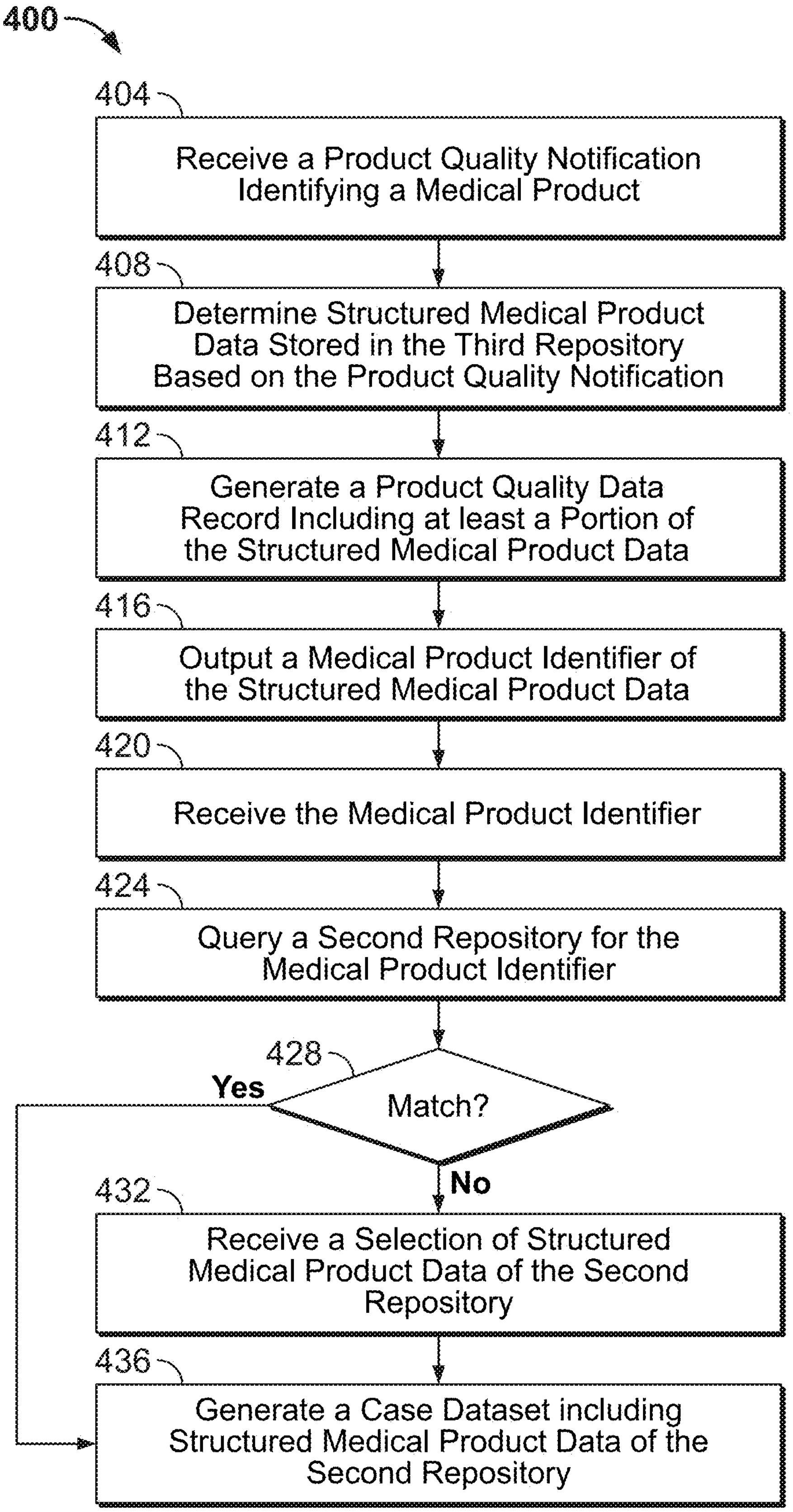
FIG. 4 may be a flow diagram of a method for determining structured data of a second repository based on an identifier of a third repository, according to an example embodiment.

Referring now to FIG. 4, a method 400 of determining structured data of a second repository based on an identifier of a third repository is shown, according to an example embodiment. Method 400 can be carried out by the system of FIG. 1. More particularly, the method 400 can be carried out by the processing circuit 128 of the provider computing system 104 and through communication with the client computing devices 108 and the health agency computing systems 112. In some embodiments, steps 404-416 are performed by the quality management circuit 148, and steps 420-436 are performed by the case intake and management circuit 142.

Method 400 commences at step 404 at which the provider computing system 104 receives a product quality notification identifying a medical product and/or a product quality issue. For instance, the product quality notification may identify or include a product quality issue (e.g., broken seal, an image of the broken seal, discolored capsule, empty syringe, etc.). Further, the product quality notification may identify a medical product and/or include medical product data (e.g., a medical product identifier, a reported medical product name, a dosage, a strength, a route of administration, etc.) associated with each medical product and/or the product quality issue. In some embodiments, the product quality notification may be received from one of the client computing devices 108 or one of the health agency computing systems 112.

In some embodiments, the product quality notification may be received in a source file. In some embodiments, the source file may be at least one of a PDF file, an Excel file, an E2B XML file, CSV file, an email, or other file types described herein. The source file or product quality notification thereof may identify or include the first medical product data, study data (e.g., a study identifier), a product quality issue, reporter data (e.g., a reporter name, a reporter country, a reporter address or contact information (e.g., email, phone number, IP address, FTP address, etc.)), patient data (e.g., patient initials, patient address or contact information), and the like.

Once the provider computing system 104 has received the product quality notification, the method 400 proceeds to step 408 at which the provider computing system 104 determines and selects structured medical product data stored in the third repository 152 based on the product quality notification. For example, the product quality notification may indicate that a medical product X was received in packaging with an open seal. Accordingly, at step 408, the provider computing system 104 may then search or query the third medical product repository 152 for structured medical product data pertaining to medical product X and return the matching structured medical product data. In some embodiments, the structured medical product data may include the second portion(s) received from the information management circuit 138, as described with regard to the method 200.

Once the provider computing system 104 has selected the structured medical product data stored in the third repository 152, the method 400 proceeds to step 412 at which the provider computing system 104 generates a product quality data record. The product quality data record may be generated to include a product quality identifier, at least a portion of the product quality notification, and at least a portion of the structured medical data. In some embodiments, after generating the product quality data record, the provider computing system 104 may store the product quality data record in a product quality data record repository (not shown).

In some embodiments, at or after step 412, the provider computing system 104 may be configured to provide the product quality data record to one or more of the health agency computing systems 112 and/or the client computing devices 108. In one example, the product quality data record may provided to one or more of the client computing devices 108 via an email. In some embodiments, the provider computing system 104 may receive an indication or request from the client computing devices 112 to provide the product quality data record to one of the health agency computing systems 112, and do so in response.

Once the first repository has generated the product quality data record, the method 300 proceeds to step 416 at which the provider computing system 104 (and more particularly the quality management circuit 148) outputs a medical product identifier of the structured medical product data. For instance, at step 416, the quality management circuit 148 may output the medical product identifier to the case intake and management circuit 142. For instance, at step 416, the quality management circuit 148, may output data associated with a potential adverse event to the case intake and management circuit 142.

In some embodiments, the quality management circuit 148 may output the medical product identifier to the case intake and management circuit 142 in response to receiving a request to do so (e.g., from one of the client computing devices 112 (see FIG. 8)). In other embodiments, the quality management circuit 148 may output the medical product identifier to the case intake and management circuit 142, in response to a specific criteria being fulfilled (e.g., the product quality data record being created and including a possible adverse event field set to true, a product quality data record entering a specific lifecycle state (e.g., submitted), the product quality data record including quality issue term that matches a specific term (e.g., "sickness," "death," etc.).

In some embodiments, at step 416, the quality management circuit 148 may output the medical product identifier and additional data (e.g., a specific date/time on which the adverse event occurred, a note or explanation of the adverse event, the adverse event term and/or code, study data or a study identifier associated with the medical product, etc.). For instance, at step 416, the quality management circuit 148 may output the medical product identifier, a product quality identifier, a description of the adverse event, a reporter name, an initial contact method of the reporter, a date of the adverse event, an awareness date, and the like.

Once the provider computing system 104 (and more particularly the quality management circuit 148) has output the medical product identifier, the method 400 proceeds to step 420 at which the provider computing system 104 (and more particularly the case intake and management circuit 142) receives the medical product identifier. For instance, the quality management circuit 148 may transmit the medical product identifier over the network 118 to the case intake and management circuit 142.

Once the provider computing system 104 (and more particularly the case intake and management circuit 142) has received the medical product identifier, the method 400 proceeds to step 424 at which the provider computing system 104 searches or queries the second repository 146 for medical product data that matches the medical product identifier. For instance, the medical product identifier may include the NDC 112233. Accordingly, the provider computing system 104 may query or search the second repository 146 for structured medical product data which matches or includes the NDC 112233.

Once the provider computing system 104 has queried the second repository 146 for the medical product identifier, the method 400 proceeds to step 428 at which the provider computing system 104 determines if there is a match. If there is no match, the method 400 proceeds to step 432 at which the provider computing system 104 receives a selection of structured medical product data of the second repository 146. For instance, in response to there being no match, the provider computing system 104 may generate and output a notification to one of the client computing devices 108. In response, the client computing device 108 may provide a selection or indication of specific structured medical product data of the second repository 146.

In some embodiments, if there is no match at step 428, the provider computing system 104 may query the second repository 146 for a secondary identifier of the medical product. For instance, at step 420, the provider computing system 104 (and more particularly the case intake and management circuit 142) may receive a secondary identifier of the medical product (e.g., a trade name of the medical product, a substance or set of substances included in the medical product, etc.). The secondary identifier may provide a back-up identifier to be used, when there is no matching medical product identifier.

After step 432, or if the provider computing system 104 determines a match at step 428, the method 400 proceeds to step 436 at which the provider computing system 104 generates a case dataset including the structured medical product data of the second repository 146. In some embodiments, the case dataset may include the additional values output by the quality management circuit 148 (e.g., the date/time, the narrative of the quality issue, etc.).

Figure 7A:
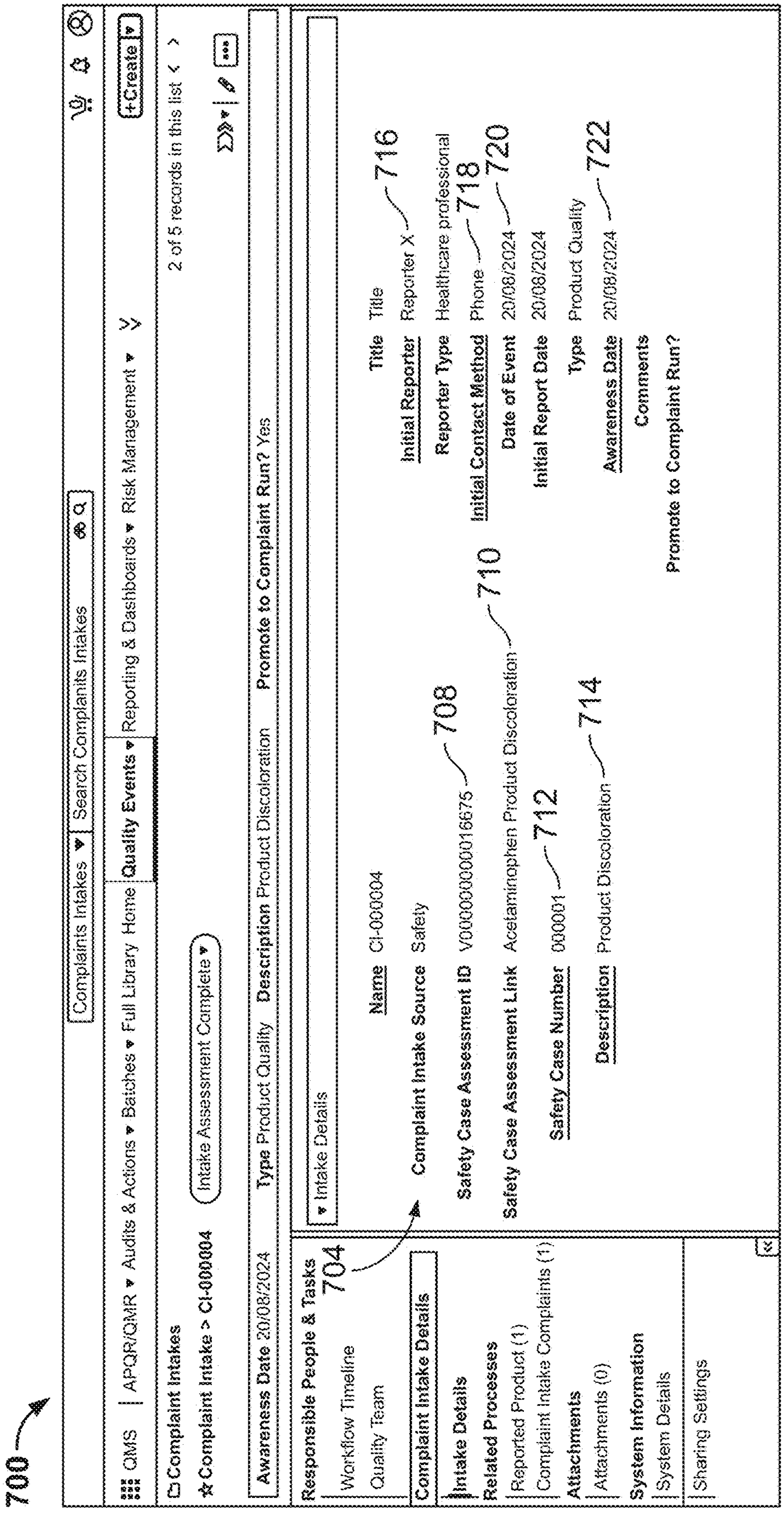
FIGS. 7A-7B may be illustrations of some aspects of a user interface generated by the data linking system of FIG. 1 to output an identifier, according to an example embodiment.
Figure 7B:
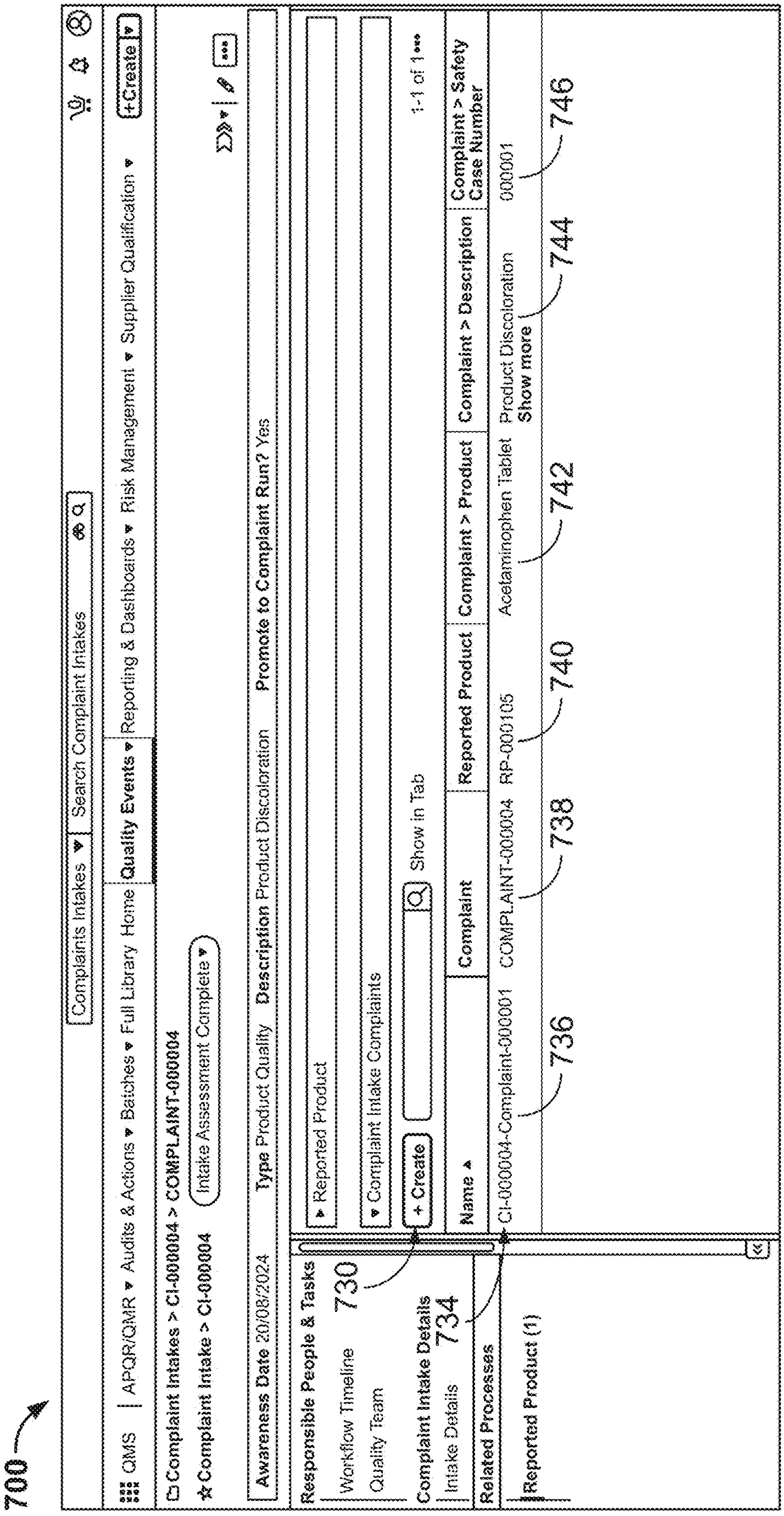

In some embodiments, after generating the case dataset, the provider computing system 104 (and more particularly the case intake and management circuit 142) may output an identifier of the case dataset (e.g., a case dataset number). For instance, FIG. 7A-7B show a complaint intake page 700 including a case ID field 746 and 712. In this regard, the provider computing system 104 (more particularly the quality management circuit 148) may add the identifier to the product quality data record for storage therein.

In some embodiments, at or after step 436, the provider computing system 104 may be configured to provide the case to one or more of the health agency computing systems 112 and/or the client computing devices 108. In one example, the case may be stored in the form of an E2B XML file and provided to one or more of the health agency computing systems 112 and/or the client computing devices 108 via an AS2 Gateway communication. In some embodiments, the provider computing system 104 may receive an indication or request from the client computing devices 112 to provide the case to one of the health agency computing systems 112, and do so in response. In some embodiments, the provider computing system 104 may automatically provide the case dataset based on a report timeframe of the case. For example, if the case is generated to include a report timeframe of seven days from receipt of the source file and it has been seven days from receipt of the source file, the provider computing system 104 may automatically provide the case to one or more of the health agency computing systems 112 and/or the client computing devices 108.

Referring now to FIGS. 5A-8, user interfaces shown and displayed to the user of the one or more client computing devices 108 during the methods 200-400 are shown, according to example embodiments. As described herein, the user interfaces of FIGS. 5A-8 may be one or more of web interfaces generated by the provider computing system 104 and rendered by each of the client computing devices 108 as part of a web application or graphical user interfaces downloaded and generated by each of the client computing devices 108 as part of a software application (e.g., a mobile application, etc.). Further, the user interfaces shown on FIGS. 5A-8 allow for communication between the user and the provider computing system 104 via the respective client computing device 108. Through interaction with the various user interfaces, the user may provide user input, feedback, and other data requested by the provider computing system 104. In this regard, it should be understood that each interaction described herein by the user with the user interfaces of FIGS. 5A-8 may be provided to one or more of the client computing devices 108 and then transmitted to the provider computing system 104 and that each action described herein as occurring to the respective client computing device 108 (e.g., navigating to a certain page, generating a popup, etc.) may be performed by the provider computing system 104.

Figure 5A:
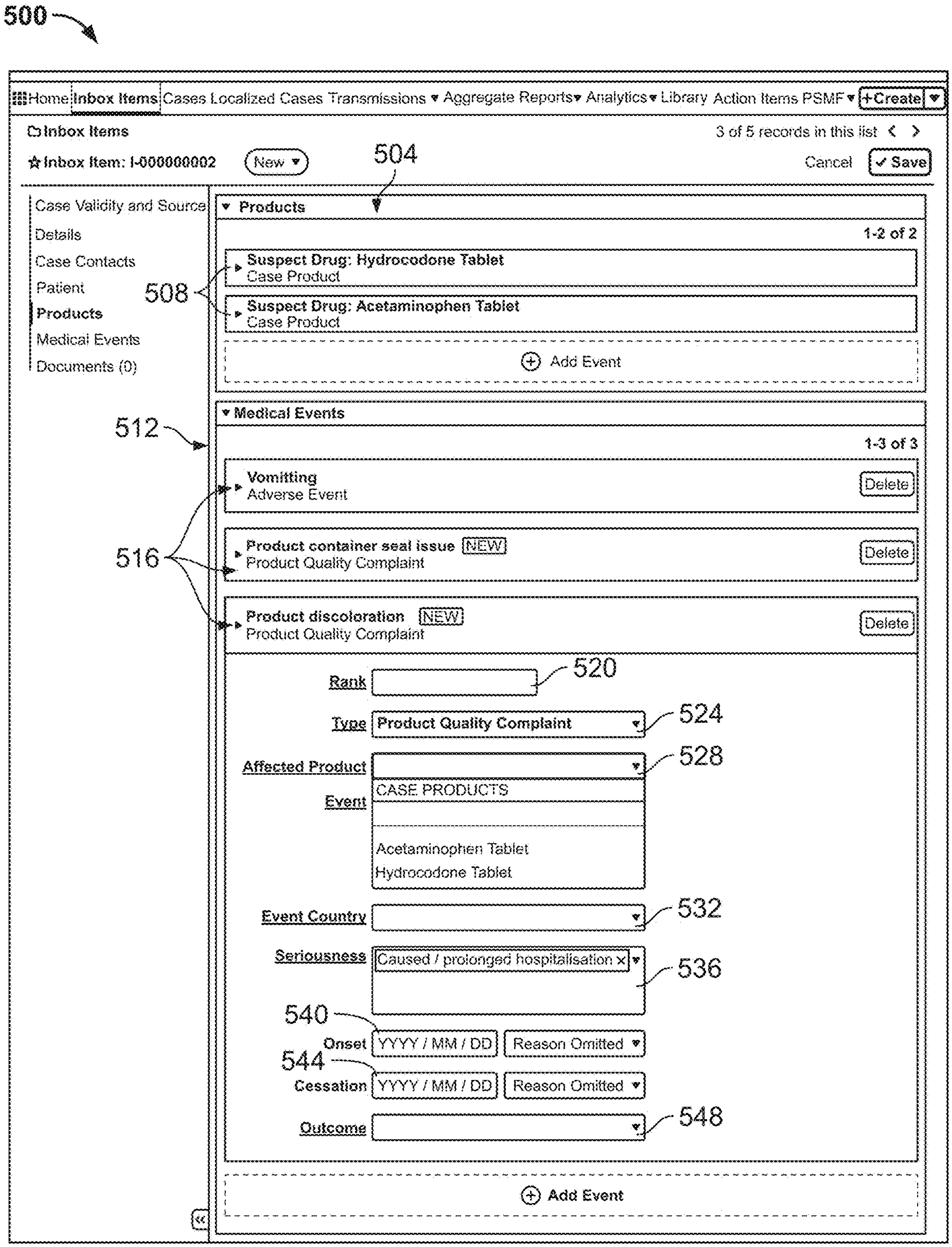
FIGS. 5A-5B may be illustrations of some aspects of a user interface generated by the data linking system of FIG. 1 to output an identifier, according to an example embodiment.
Figure 5B:
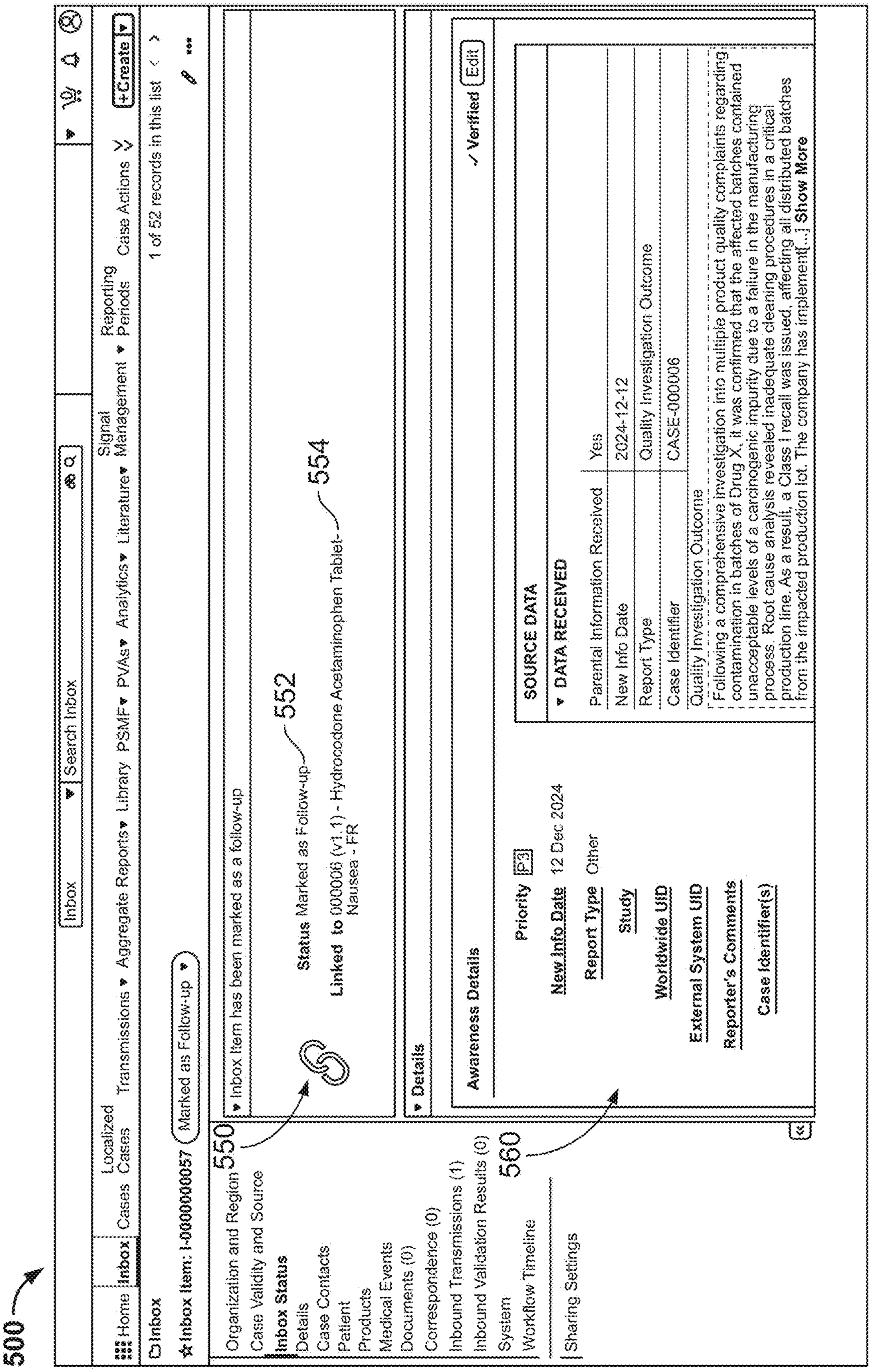

Referring now to FIGS. 5A-5B, an inbox item or adverse event page 500 which can be displayed on a display the I/O circuit 180 of the client computing device 112, is shown. In general, the adverse event page 500 provides the user an interface to view, modify, and select adverse event data of a specific source file. As shown, the adverse event page 500 includes the product(s) section 504, the adverse event(s) section 516, the follow-up section 550, and the details section 560. To render or generate the adverse event page 500 on the client computing device 112, the provider computing system 104 may provide the source file and the adverse event data of the source file to the client computing device 112. In this regard, it should be understood that each of the sections, fields, or buttons of the adverse event page 500 may include adverse event data.

The products section 504 may include multiple product representations 508 that identify the medical product of the adverse event data. Likewise, the event section 516 includes multiple adverse event representations 516 that my each include a rank field 520, a type field 524, a affected product field 528, an adverse event term field (not shown), a country field 532,a seriousness field 536, a date of onset field 540, a date of cessation field 544, and an outcome field 548. The type field 524 may be a selectable field to indicate a type of the adverse event, including a product quality complaint option, which indicates the adverse event is associated with a product quality complaint.

The follow-up section 550 may include fields associated with a related case including a status field 552 and a linked case field 554. The linked case field 554 may include a link to the case associated with the follow-up case, as described herein. Likewise, the details section 560 may include general details or adverse event data.

Figure 6A:
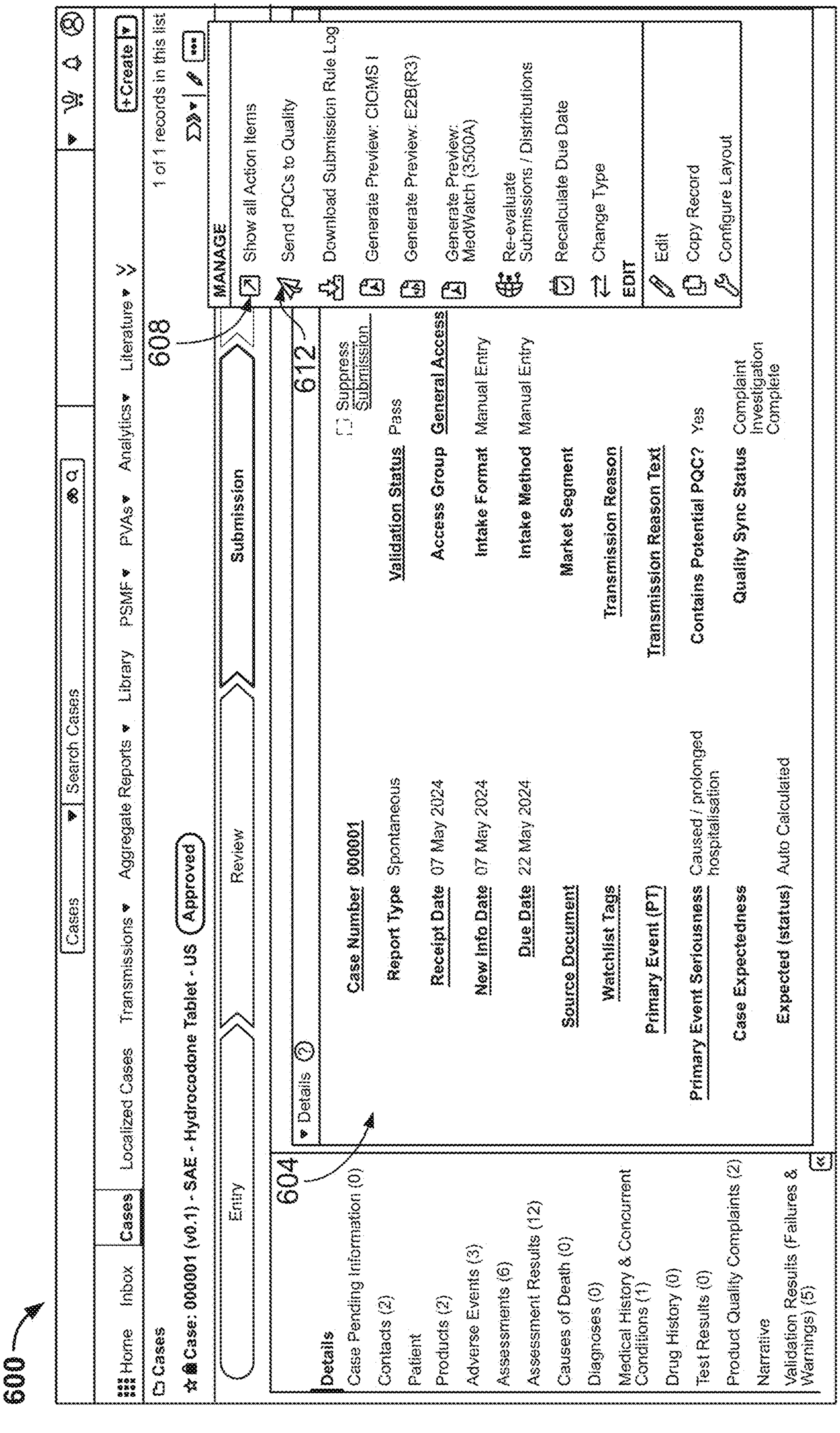
FIGS. 6A-6B may be illustrations of some aspects of a user interface generated by the data linking system of FIG. 1 to manage a case dataset, according to an example embodiment.
Figure 6B:
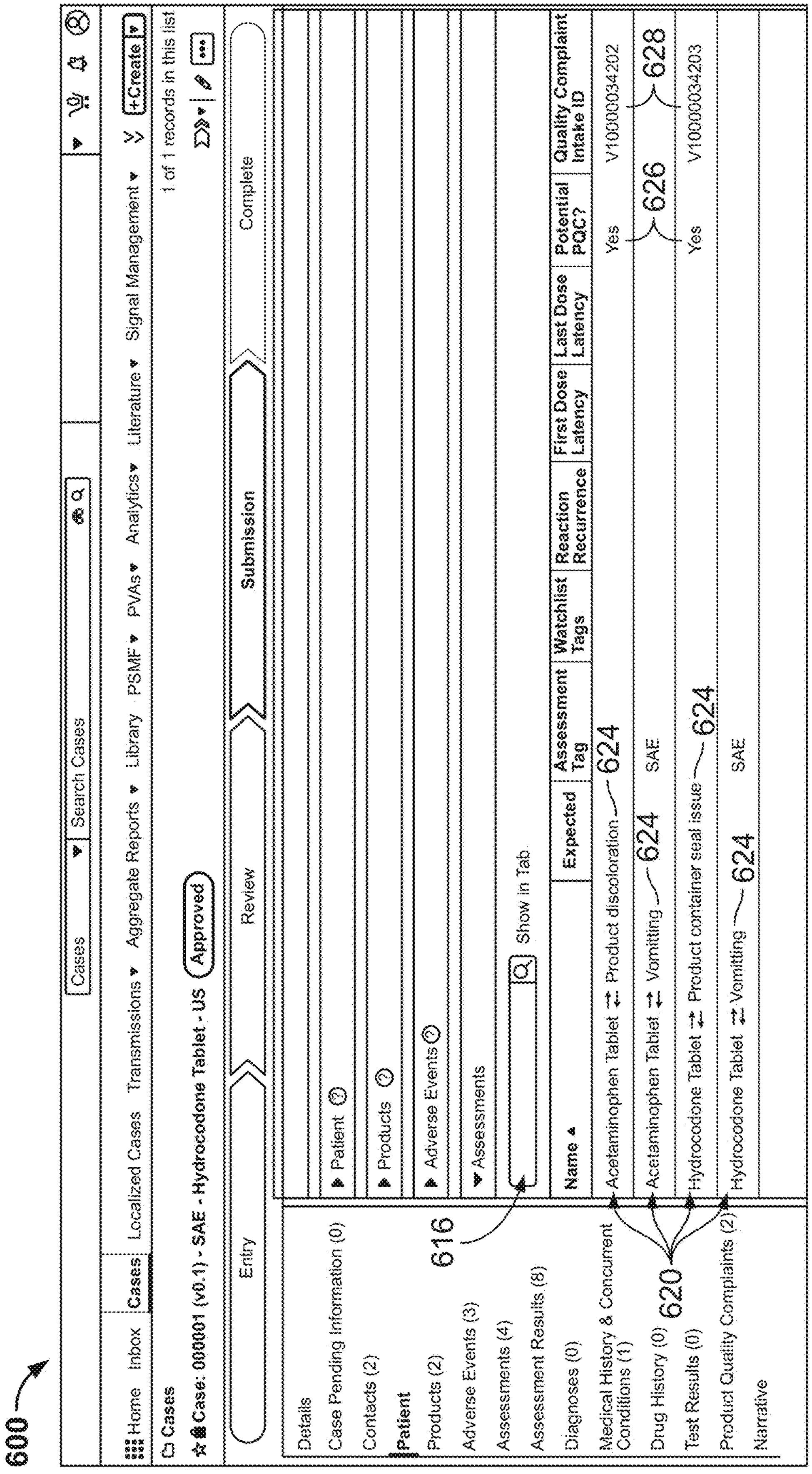

Referring now to FIGS. 6A-6B, a case page 600 which can be displayed on a display the I/O circuit 180 of the client computing device 112, is shown. In general, the case page 600 provides the user an interface to view, modify, and select case data of a specific case dataset. As shown, the case page 600 includes details section 604, the options menu 608, and the assessments section 616. To render or generate the case page 600 on the client computing device 112, the provider computing system 104 may provide the case dataset and the case data of the case dataset to the client computing device 112. In this regard, it should be understood that each of the sections, fields, or buttons of the case page 600 may include case data (e.g., medical product data, an adverse event identifier, etc.).

The options menu 608 may be a selectable menu that includes multiple options associated with the case dataset of the case page 600 including a send button or option 612. The send button 612 may be a selectable button or option that, when selected, causes the client computing device 112 to send a notification to the provider computing system 104 to output the medical product identifier from the case intake and management circuit 142 to the quality management circuit 148 (e.g., step 316).

The assessments section 616 may include an assessment representation 620 associated with each medical product and adverse event pair. Likewise, each assessment representation 620 may include a name field 624, a potential product quality complaint field 626, and a product quality data record identifier field 628. When a medical product identifier is output to the quality management circuit 148, the quality management circuit 148 may send back a product quality identifier, which may populate the product quality data record identifier field 628.

Referring now to FIGS. 7A-7B, a product quality notification page 700 which can be displayed on a display the I/O circuit 180 of the client computing device 112, is shown. In general, the product quality notification page 700 provides the user an interface to view, modify, and select data of a product quality notification. As shown, the product quality notification page 700 includes details section 704 and a complaint intake section 730. To render or generate the product quality notification page 700 on the client computing device 112, the provider computing system 104 may provide the product quality notification and the data thereof to the client computing device 112. In this regard, it should be understood that each of the sections, fields, or buttons of the product quality notification page 700 may include data of the product quality notification (e.g., medical product data, a product quality issue, etc.).

The details section 704 may include general details of the product quality notification including a case identifier field 708, a case dataset link field 710, a case number field 612, a description field 714, an initial reporter field 716, an initial contact method field 718, a date of event field 720, and an awareness date field 722. In some embodiments, each of the underlined fields are data or fields that may be received from the case intake and management circuit 142. Likewise, the case identifier field 708 may include an identifier of the case dataset from which the data of the product quality notification page 700 came. Likewise, the case dataset link field 710 may include a link to the case dataset.

The complaint intake section 730 may include one or more complaint intake representations 734 which identify the case dataset(s) from which the data of the product quality notification page 700 was received. In this regard, each complaint intake representation 734 may include a name field 736, a complaint field 738, a medical product identifier field 740, a complaint product field 742, a complaint description 744, and a case number field 746. The medical product identifier field 740 may include the medical product identifier used to link the medical product across the various systems described herein.

Figure 8:
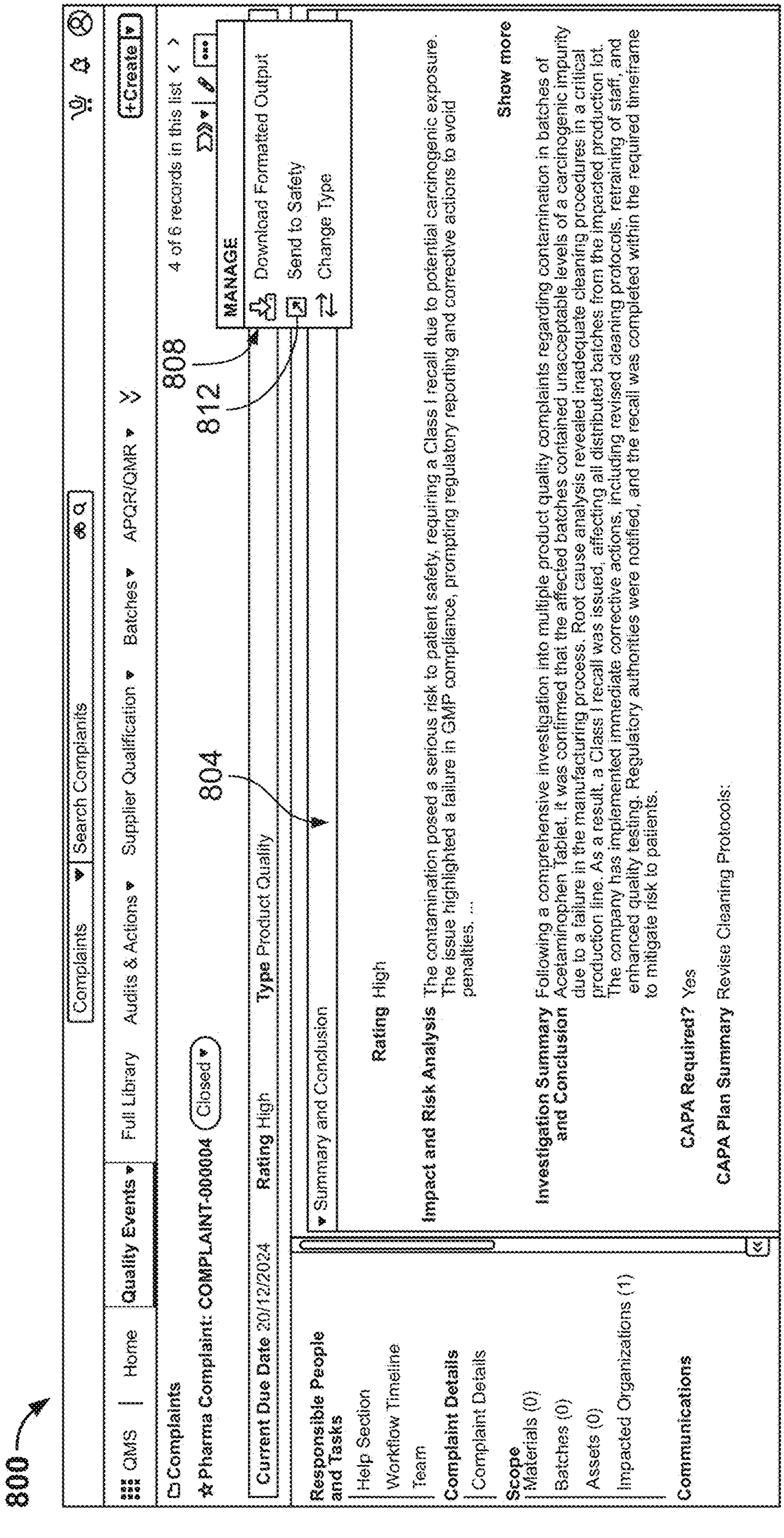
FIG. 8 may be an illustration of some aspects of a user interface generated by the data linking system of FIG. 1 to manage a product quality data record, according to an example embodiment.

Referring now to FIG. 8, a product quality data record page 800 which can be displayed on a display the I/O circuit 180 of the client computing device 112, is shown. In general, the product quality data record page 800 provides the user an interface to view, modify, and select data of a product quality data record. As shown, the product quality data record page 800 includes a summary section 804 and an option menu 808. To render or generate the product quality data record page 800 on the client computing device 112, the provider computing system 104 may provide the product quality data record and the data thereof to the client computing device 112. In this regard, it should be understood that each of the sections, fields, or buttons of the product quality data record page 800 may include data of the product quality data record (e.g., medical product data, a product quality issue, etc.).

The summary section 804 may include a summary of the product quality issue. Likewise, the options menu 808 may be a selectable menu that includes multiple options associated with the product quality data record of the product quality data record page 800 including a send button or option 812. The send button 812 may be a selectable button or option that, when selected, causes the client computing device 112 to send a notification to the provider computing system 104 to output the medical product identifier from the quality management circuit 148 to the case intake and management circuit 142 (e.g., step 416).

The embodiments described herein have been described with reference to the drawings. The drawings illustrate certain details of specific embodiments that implement the systems, methods, and programs described herein. However, describing the embodiments with drawings should not be construed as imposing on the disclosure any limitations that may be present in the drawings.

It should be understood that no claim element herein is to be construed under the provision of 35 U.S.C § 112 (f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexors, registers, capacitors, inductors, diodes, wiring, and so on.

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other embodiments, two or more processors may be coupled via a bus to enable independent, parallel, pipelined, or multi-threaded instruction execution. Each processor may be implemented as one or more general purpose processors, application specific integrated circuits (ASICs), field programmable gate arrays (FPGAs), digital signal processors (DSPs), or other suitable electronic data processing components structured to execute instructions provided by the memory. The one or more processors may take the form of a single core processor, a multi-core processor (e.g., dual core, quad core, etc.), microprocessor, etc. In some embodiments, the one or more processors may be external to the apparatus. For example, the one or more processors may be a remote processor (e.g., a cloud-based processor). Alternatively or additionally, the one or more processors may be internal and/or local to the apparatus. In this regard, a circuit or components thereof may be disposed locally (e.g., as part of a local server, a local computing system) or remotely (e.g., as part of a remote server such as a cloud-based server). To that end, a "circuit" as described herein may include components that are distributed across one or more locations. Further, each of the circuits described herein may be distributed across one or more locations (e.g., each as part of one or more remote servers).

An example system for implementing the overall system or portions of the embodiments might include a general-purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile storage media may take the form of ROM, flash memory (e.g., flash memory such as NAND, 3D NAND, NOR, 3D NOR), EEPROM, MRAM, magnetic storage, hard disks, optical disks, etc. Combinations of the above are also included within the scope of machine-readable media. In this regard, machine-executable instructions comprise, for example, instructions and data which cause a general-purpose computer, special purpose computer, or special purpose processing machine to perform a certain function or group of functions. Each respective memory device may be operable to maintain or otherwise store data relating to the operations performed by one or more associated circuits, including processor instructions and related data (e.g., database components, object code components, script components), in accordance with the example embodiments described herein.

It should also be noted that the term "input devices," as described herein, may include any type of input device including, but not limited to, a keyboard, a keypad, a mouse, a joystick, or other input devices performing a similar function. Comparatively, the term "output device," as described herein, may include any type of output device including, but not limited to, a computer monitor, printer, facsimile machine, or other output devices performing a similar function.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Other substitutions, modifications, changes, and omissions may be made in the design, operating conditions and embodiment of the embodiments without departing from the scope of the present disclosure as expressed in the appended claim.

What is claimed is:

1. A method for linking structured data across a first repository of a first circuit and a second repository of a second circuit, the method comprising:

receiving, by a first circuit associated with a first application, adverse event data including an adverse event code and identifying a medical product;

querying, by the first circuit, the first repository based on the adverse event data to select first structured medical product data of the first repository, wherein the first structured medical product data includes an identifier, and wherein the first structured medical product data is associated with a first data structure;

generating, by the first circuit, a case dataset including the adverse event code and at least a portion of the first structured medical product data;

outputting, by the first circuit, the identifier of the first structured medical product data;

receiving, by a second circuit associated with a second application, the identifier;

querying, by the second circuit, the second repository based on the identifier to select second structured medical product data of the second repository, wherein the second structured medical product data includes the identifier, and wherein the second structured medical product data is associated with a second data structure; and generating, by the second circuit, a product quality data record including at least a portion of the second structured medical product data.

2. The method of claim 1, further comprising:

outputting, by a third circuit associated with a third application, third structured medical product data of a third repository for storage in the first repository, wherein the third structured medical product data includes the identifier, and wherein the third structured medical product data is associated with a third data structure;

modifying, by the first circuit, the third structured medical product data to match the first data structure; and storing, by the first repository, the modified third structured medical product data.

3. The method of claim 2, further comprising:

outputting, by the third circuit, the third structured medical product data for storage in the second repository, modifying, by the second circuit, the third structured medical product data to match the second data structure; and storing, by the second repository, the modified third structured medical product data.

4. The method of claim 3, wherein the third application is a Regulatory Information Management (RIM) application.

5. The method of claim 1, wherein the case dataset includes a case identifier, and wherein the first circuit outputs the identifier of the first structured medical product data and the case identifier.

6. The method of claim 4, further comprising:

receiving, by the second circuit, additional data;

modifying, by the second circuit, the product quality data record to include the additional data; and outputting, by the second circuit, the additional data and the case data identifier.

7. The method of claim 5, wherein the case dataset is a first case dataset, and wherein the method further comprises:

receiving, by the first circuit, the additional data and the case data identifier; and generating, by the first circuit, a second case dataset including the case identifier, at least a portion of the additional data, and a link to the first case dataset.

8. The method of claim 1, wherein the first application is a pharmacovigilance individual case safety report (ICSR) reporting application.

9. The method of claim 1, wherein the second application is a product quality application.

10. A method for linking structured data across a first repository of a first circuit and a second repository of a second circuit, the method comprising:

receiving, by a first circuit associated with a first application, a product quality notification identifying a product quality issue and a medical product;

querying, by the first circuit, the first repository based on the product quality notification to select first structured medical product data of the first repository, wherein the first structured medical product data includes an identifier, and wherein the first structured medical product data is associated with a first data structure;

generating, by the first circuit, a product quality data record including at least a portion of the first structured medical product data;

outputting, by the first circuit, the identifier of the first structured medical product data;

receiving, by a second circuit associated with a second application, the identifier;

querying, by the second circuit, the second repository based on the identifier to select second structured medical product data of the second repository, wherein the second structured medical product data includes the identifier, and wherein the second structured medical product data is associated with a second data structure; and generating, by the second circuit, a case dataset including at least a portion of the second structured medical product data.

11. The method of claim 10, further comprising:

outputting, by a third circuit associated with a third application, third structured medical product data of a third repository for storage in the first repository, wherein the third structured medical product data includes the identifier, and wherein the third structured medical product data is associated with a third data structure;

modifying, by the first circuit, the third structured medical product data to match the first data structure; and storing, by the first repository, the modified third structured medical product data.

12. The method of claim 11, further comprising:

outputting, by the third circuit, the third structured medical product data for storage in the second repository, modifying, by the second circuit, the third structured medical product data to match the second data structure; and storing, by the second repository, the modified third structured medical product data.

13. The method of claim 12, wherein the third application is a Regulatory Information Management (RIM) application.

14. The method of claim 10, wherein the case dataset includes a case identifier, and wherein the second circuit outputs the case identifier.

15. The method of claim 14, further comprising:

receiving, by the first circuit, additional data;

modifying, by the first circuit, the product quality data record to include the additional data; and outputting, by the first circuit, the additional data and the case data identifier.

16. The method of claim 14, wherein the case dataset is a first case dataset, and wherein the method further comprises:

receiving, by the second circuit, the additional data and the case data identifier; and generating, by the second circuit, a second case dataset including the case identifier, at least a portion of the additional data, and a link to the first case dataset.

17. The method of claim 10, wherein the second application is a pharmacovigilance individual case safety report (ICSR) reporting application.

18. The method of claim 10, wherein the first application is a product quality application.

19. The method of claim 10, wherein the product quality data record includes a product quality identifier, and wherein the first circuit outputs the identifier and the product quality identifier.

20. A method for linking structured data across a first repository of a first circuit and a second repository of a second circuit, the method comprising:

receiving, by a first circuit associated with a first application, adverse event data including an adverse event code and identifying a medical product;

querying, by the first circuit, the first repository based on the adverse event data to select first structured medical product data of the first repository, wherein the first structured medical product data includes an identifier, and wherein the first structured medical product data is associated with a first data structure;

generating, by the first circuit, a first case dataset including the adverse event code, a case identifier, and at least a portion of the first structured medical product data;

outputting, by the first circuit, the identifier of the first structured medical product data and the case identifier;

receiving, by a second circuit associated with a second application, the identifier and the case identifier;

querying, by the second circuit, the second repository based on the identifier to select second structured medical product data of the second repository, wherein the second structured medical product data includes the identifier, and wherein the second structured medical product data is associated with a second data structure;

generating, by the second circuit, a product quality data record including at least a portion of the second structured medical product data;

outputting, by the second circuit, the case identifier;

receiving, by the first circuit, the case data identifier; and generating, by the first circuit, a second case dataset including the case identifier and a link to the first case dataset.

* * * * *